US006171804B1

(12) United States Patent
Cowburn et al.

(10) Patent No.: US 6,171,804 B1
(45) Date of Patent: Jan. 9, 2001

(54) METHOD OF DETERMINING INTERDOMAIN ORIENTATION AND CHANGES OF INTERDOMAIN ORIENTATION ON LIGATION

(75) Inventors: David Cowburn, Westfield, NJ (US); Rong Xu, Tarrytown; David Fushman, New York, both of NY (US)

(73) Assignee: The Rockefeller University, New York, NY (US)

( * ) Notice: Under 35 U.S.C. 154(b), the term of this patent shall be extended for 0 days.

(21) Appl. No.: 09/351,570

(22) Filed: Jul. 12, 1999

(51) Int. Cl.[7] ........................ G01N 33/53; G01N 33/566; G01N 33/557
(52) U.S. Cl. ........................ 435/7.1; 436/501; 436/517
(58) Field of Search ........................ 435/6, 69.1, 91.2; 436/173; 324/309, 316

(56) References Cited

U.S. PATENT DOCUMENTS

| 5,698,401 | 12/1997 | Fesik et al. . |
| 5,804,390 | 9/1998 | Fesik et al. . |
| 5,891,643 | 4/1999 | Fesik et al. . |

OTHER PUBLICATIONS

Xu et al., "Determining RNA solution structure by segmental isotopic labeling an NMR: Application to Caenorhabditis elegans spliced leader RNA 1," Proceedings of National Academy of Science USA, Jan. 1996, vol. 93, pp. 44–48.*
Hajduk et al., "NMR–Based Discovery of Lead Inhibitors That Block DNA Binding of the Human Papilomavirus E2 Protein," Journal of Medicinal Chemistry, 1997, vol. 40, pp. 3144–3150.*
Anderrson et al.,*Science*; 250:979–982 (1990).
Broadhurst et al, *Biochemistry*, 34:16608–17 (1995.
Bruschweiler et al., *Science*, 268:886–9 (1995).
Bugg et al., *Scientific American*, Dec.:92–98 (1993).
Camobell and Downing, *Nat. Struct. Biol.*, 5 Suppl.:469–9 (1998).
Cantley et al., *Cell* 64:281–302 (1991).
Chong et al., *Gene* 271–281 (1997).
Clore et al., *J. Am. Chem. Soc.*, 120:4889–90 (1998).
Clore et al., *J. Am. Chem. Soc.*, 120:10571–2 (1988).
Deininger and Goldman, *Curr. Opin. Hematol.*, 5:302–8 (1998).
Dunbrack et al., *Folding & Design* , 2:27–42 (1997).
Fushman and Cowburn, *J. Biomol. NMR*, 13:139–147.
Fushman and Cowburn, *J. Am. Chem. Soc.*, 120:7109–10 (1998).
Goff et al. *Cell* 22:777–785 (1980).
Gosser et al., *Structure*, 3:1075–1086 (1995).
Koch et al., *Science*: 252:668–674 (1991).
Koleske, *Neuron* 21:1259–1272 (1998).
Kraulis, *J. Appl Crystallogr.* 24:946–950 (1991).
Kuriyan and Cowburn, *Annu. Rev. Biophys. Biomol. Struct.*, 26:259–288 (1997).
Lam et al., *Science* 263:380–384 (1994).
Mayer et al., *Nature* 332:272–275 (1988).
Nam et al., *Structure* 4:1105–1114 (1996).
Pervushin et al., *Proc. Natl. Acad. Sci. U.S.A.*, 94:12366–71 (1997).
Ponting, *Nucleic Acid Res.* 27:229–232 (1999).
Sadowski et al., *Mol. Cell. Biol.* 6:4396–4408 (1986).
Sass et al., *J. Am. Chem. Soc.*, 121:2047–55 (1999).
Schlessinger et al., *Neuron* 9:383–391 (1992).
Scott and Smith, *Science*, 249:386–390 (1990).
Severinov et al., *J. Biol. Chem.* 273:16205–16209 (1998).
Shultz *Proc. Natl. Acad. Sci. USA* 95:5857–5864 (1998).
Sicheri and Kuriyan, *Curr, Op, Str. Biol.* 7: 777–785 (1997).
Songyang et al., *Cell* 72:767–778 (1993).
Tjandra and Bax, *Science*, 278:1111–4.
Tolman et al., *Proc. Natl. Acad.. Sci., U.S.A.*, 92:9279–83 (1995).
Woessner, *J. Chem. Phys.*, 37:647–654 (1962).
Xu et al., *Proc. Natl. Acad. Sci. U.S.A.*, 96:388–393 (1999).
Xu et al., *Biochemistry*, 38:3491–97 (1999).
Yamazaki et al., *J. Amer. Cem. Soc.* 120:5591–5592 (1998).
Yu, *Proc. Natl. Acad. Sci. USA* 96:332–334 (1999).

\* cited by examiner

Primary Examiner—John S. Brusca
Assistant Examiner—Young Kim
(74) Attorney, Agent, or Firm—Klauber & Jackson

(57) ABSTRACT

The present invention provides methods for determining the relative orientation of the individual components of a macromolecule in solution with respect to the global molecular coordinate frame of the macromolecule. The present invention further provides methods for applying this structural information, including for rational drug design.

22 Claims, 5 Drawing Sheets

METHOD OF DETERMINING INTERDOMAIN ORIENTATION AND CHANGES OF INTERDOMAIN ORIENTATION ON LIGATION

GOVERNMENTAL SUPPORT

The research leading to the present invention was supported, at least in part, by a grant from the National Institutes of Health, Grant No. GM-47021. Accordingly, the Government may have certain rights in the invention.

FIELD OF THE INVENTION

The present invention pertains to methods for determining the relative orientation of the individual components of a macromolecule with respect to the global molecular coordinate frame of the macromolecule. Such methods can be used to determine the structure of multicomponent molecules.

BACKGROUND OF THE INVENTION

Knowledge of the detailed three-dimensional structure of any given macromolecule is critical for optimizing and/or regulating the use of that macromolecule, be it a protein that is malfunctioning in a metabolic pathway, or a synthetic polymer used in microchip technology. Currently, there are two major strategies for determining the detailed three-dimensional structure of a macromoleucle: X-ray crystallography and nuclear magnetic resonance. X-ray crystallographic analysis requires the time-consuming process of preparing high quality crystals, whereas classical NMR three-dimensional analysis is limited to macromolecules that are under 35 kilodaltons [Yu, Proc. Nat. Acad. Sci. USA 96:332–334 (1999)]. Furthermore, such methods of high-resolution structure determination are generally applicable to macromolecules formed by tight contacts between the individual, well-structured components of the macromolecule. These methods have more limited applicability in those cases where there are weaker interactions between the component; examples include the relatively transient associations formed in complexes involved in signal transduction, or in transcriptional control. Crystal structures of such complexes might be biased by packing forces comparable to the interdomain interactions, while the precision and accuracy of the conventional NMR structural approaches are necessarily limited by the restricted number of nuclear Overhauser effect (NOE) contacts and by inter-domain flexibility rendering the available NOE information uninterpretable.

Recently proposed NMR approaches [Tolman et al., Proc. Natl. Acad. Sci., U.S.A., 92:9279–83 (1995); Bruschweiler et al., Science, 268:886–9 (1995); Broadhurst et al., Biochemistry, 34:16608–17 (1995); Tjandra et al., Nat. Struct. Biol., 4:443–9 (1997); and Tjandra and Bax, Science, 278:1111–4] are potentially capable of improving both the accuracy and precision of structure determination in solution and might prove to be the method of choice in those cases when the number of available short-range NOE contacts is limited. These methods are based on 'long-range' structural information in the form of inter-nuclear vector constraints with respect to an overall, molecular reference frame. These constraints may arise from correlation with the anisotropic hydrodynamic properties of the molecule [Bruschweiler et al., Science, 268:886–9 (1995); Broadhurst et al, Biochemistry, 34:16608–17 (1995); and Tjandra et al, Nat. Struct. Biol., 4:443–9 (1997)], or from weak alignment of molecules in solution caused by either their interaction with the magnetic field [Tolman et al., Proc. Natl. Acad. Sci, U.S.A., 92:9279–83 (1995)] or by the liquid crystalline characteristics of the medium [Tjandra and Bax, Science, 278:1111–4]. The NMR relaxation approach [Bruschweiler et al., Science, 268:886–9 (1995); Broadhurst et al., Biochemistry, 34:16608–17; and Tjandra et al, Nat. Struct. Biol., 4:443–9 (1997)] which takes advantage of the anisotropic character of the overall rotation, is most generally applicable to a wide range of macromolecules in their native milieu. The magnetic alignment method [Tolman et al., Proc. Natl. Acad. Sci., U.S.A., 92:9279–83 (1995) and Tjandra et al., Nature Structural Biology, 4:732 (1997)] requires macromolecules to possess a sufficiently high anisotropy of the magnetic susceptibility, and is not, therefore, widely applicable. The approaches based on weak alignment of macromolecules in liquid crystalline medium may be restricted by possible interactions between the molecule under investigation and the medium. For a list of intractable target proteins by this method using lipid bicelles see footnote 8 in Clore et al.,[ J. Am. Chem. Soc., 120:10571–2 (1998)], although more recent alignment methods may alleviate this issue [Clore et al., J. Am. Chem. Soc., 120:10571–2 (1998); Hansen et al., J. Am. Chem. Soc., 120:11210–11 (1998); Koenig et al., J. Am. Chem. Soc., 121:1385–6 (1999); and Sass et al., J. Am. Chem. Soc., 121:2047–55 (1999)].

Naturally occurring polymers such as nucleic acids and proteins are macromolecules that have distinct three-dimensional structures. Indeed, the ability of any given protein to carry out its physiological role, regardless of whether it functions as a structural element, a binding partner, and/or a biochemical catalyst, requires that the protein assume a specific conformation. This conformation is dependent on the three-dimensional folding of the protein into specific domains and the orientation of these domains to each other, as well to the corresponding domains of other proteins.

The binding of a ligand to a protein (e.g., a substrate to an enzyme), generally results in a local alteration of the three-dimensional structure of the protein. In addition, the binding of the ligand to one site of a protein, can also alter the structure of other regions of the polypeptide [See generally, Kempner, FEBS 326:4–10 (1993)]. Indeed the relative orientation and motions of domains within many proteins are key to the control of multivalent recognition, or the assembly of protein-based cellular machines. Therefore, it is not surprising that there has been a long and continuous effort to determine the structures of nucleic acids and proteins, not only in their resting state, but also in their more dynamic state in their native environment.

In recent years it has become apparent that there is a large but finite number of protein structural domains that are shared throughout nature. These domains are used by the proteins to carry out their biological roles. One such pair of domains are the src homology domains SH2 and SH3. Eukaryotic cellular signal-transduction pathways that are initiated by transmembrane receptors with associated tyrosine kinases rely on these two small protein domains for mediating many of the protein-protein interactions that are necessary for transmission of the signal [Cantley et al., Cell 64:281–302 (1991); Schlessinger et al., Neuron 9:383–391 (1992); Pawson et al., Curr. Biol. 3:434–442 (1993)]. These domains were first discovered in cytoplasmic (non-receptor) protein tyrosine kinases such as the src oncogene product, thus leading to the term 'src homology domains' [Sadowski et al., Mol. Cell. Biol. 6:4396–4408 (1986)].

The unique importance of these domains became clear with the discovery of the crk oncogene product, which consists of little more than an SH2 and an SH3 domain fused to the viral gag protein, but is capable of transforming cells [Mayer et al,. *Nature* 332:272–275 (1988)]. SH2 and SH3 domains have been identified in molecules with distinct functions that act downstream from the receptors for, among others, epidermal growth actor (EGF), platelet-derived growth factor (PDGF), insulin and interferon, and the T-cell receptor [Koch et al., *Science*: 252:668–674 (1991)].

An important aspect of the role of protein domains such as the SH2 and SH3 domains is their ability to recognize particular amino acid sequences in their target proteins: SH2 domains bind tightly to phosphorylated tyrosine residues [Anderrson et al., *Science*; 250:979–982 (1990); Matsuda et al. *Science* 248:1537–1539 (1990); Moran et al. *Proc. Natl. Acad. Sci.* USA 87:8622–8626 (1990); Mayer et al *Proc. Natl. Acad. Sci.* USA: 88:627–631 (1991); Songyang et al. *Cell* 72:767–778 (1993)] whereas SH3 domains bind to proline rich segments forming a short helical turn in the complexes [Kuriyan and Cowburn, *Annu. Rev. Biophys. Biomol. Struct.*, 26:259–288 (1997), the contents of which are hereby incorporated herein by reference in its entirety]. The modular nature of these domains is made clear by the fact that they occur in different positions in the polypeptide chains of the intact proteins of which they are a part, and that the binding functions can often be reproduced by isolated domains. Although SH2 and SH3 domains frequently occur close together in sequence, some proteins have only one or the other domain, and some have more than one version of either domain. Proteins that contain more than one of these domains do not always maintain a strict spacing or particular order between the domains.

Even for the SH2 and SH3 domains for which the individual structural properties and ligand specificities are fairly well understood, the structural organization and interactions between them in the multidomain complexes are complex, and difficult to elucidate. These interactions are likely to be of significance, in particular, in view of the frequency of protein constructs containing adjacent SH2 and SH3 domains. Examples of structural studies of the multiple SH3/SH2 domain constructs are the Abelson protein tyrosine kinase SH(32) or Abl SH(32); Lck SH(32); Grb2 SH(323); Hck SH(321); Src and Src SH(32) [reviewed in Kuriyan and Cowburn, *Annu. Rev. Biophys. Biomol. Struct.*, 26:259–288 (1997); and Sicheri and Kuriyan, *Curr. Opin. Str. Biol.*, 7:777–785 (1997)]. Structural approaches to these complexes are complicated by the limited contacts and energies of the interdomain interactions. While the crystal structures of the src-family SH(321) kinase systems have shed significant insight into unexpected kinases/SH3 interactions, and demonstrated the allosteric nature of kinase inhibition by intramolecular phosphorylation, these structures of the down-regulated, inactive forms of the enzymes do not provide a detailed understanding of the mechanism of regulation, or the roles of domains in substrate recognition [Sicheri and Kuriyan, *Curr. Opin. Str. Biol.*, 7:777–785 (1997) and Mayer et al., *Current Biology*, 5:296–305 (1995)]. This issue of interdomain flexibility in solution is a general one for large multidomain proteins [Campbell and Downing, *Nat. Struct. Biol.*, 5 Suppl.:496–9 (1998)].

Therefore, there is a need for determining the structural organization and interactions of components of macromolecules including monitoring enzymatic reactions, DNA-protein interactions, ligand binding, and protein folding. Furthermore, there is a need to exploit such determinations in order to be able to design more potent drugs, pharmaceutical therapies and diagnostic agents. In addition, there is a need to further elucidate the complex structural characteristics of synthetic chemical polymers in solution.

The citation of any reference herein should not be construed as an admission that such reference is available as "Prior Art" to the instant application.

SUMMARY OF THE INVENTION

The present invention provides methods for determining the relative orientation of the individual components of a macromolecule with respect to the global molecular coordinate frame of the macromolecule. Such determinations both complement and extend the currently known methods of calculating the three dimensional structures of macromolecules. Therefore, the methods disclosed herein can be performed alone or in conjunction with other structural determinations including conventional methods of structure determination that use local constraints (interatomic distances, torsion angles, and/or hydrogen bonds). In addition, the methods of structural analysis provided herein can be performed in conjunction with synthetic structural refinements of the individual components of the macromolecule in order to design and construct modified macromolecules that have improved and/or more desirable properties. Furthermore, the present invention provides methods of identifying and/or designing ligands to the macromolecules that have improved and/or more desirable properties.

The present invention therefore provides a method for determining the orientation of the molecular frame for two or more selected components of a macromolecule that contains two or more individual components. The rotational diffusion axes for the selected components are determined. The inter-component orientation in the macromolecule can be determined based on the orientation of each individual selected component with respect to the global frame, and the rotational diffusion axes of the selected components are aligned. In a preferred embodiment the orientation of the molecular frame for each individual selected component of the macromolecule is determined by determining the orientation of the overall rotational diffusion tensor as seen by each of the selected components.

The present invention further provides a method of determining the change in orientation of the selected components of a macromolecule in solution upon binding of a ligand to the macromolecule. One such embodiment comprises measuring the relaxation rate of a nucleus contained by a selected macromolecule component in the presence of a ligand for the macromolecule under conditions that the ligand binds to the macromolecule. The relaxation rate is substantially determined by the geometric and electronic properties of the nucleus in its bond to hydrogen isotope(s). The relaxation rate can then be referred to as the relaxation rate of the heteronuclear bond. This relaxation rate of the heteronuclear bond is measured in the absence of the ligand under otherwise the same conditions. The overall hydrodynamic characteristics and the local internuclear vector orientation of the selected components of the macromolecule are then derived for the macromolecule in the presence and absence of the ligand. The change in orientation of the selected components of the macromolecule in solution upon binding of the ligand is thus determined. In a preferred embodiment the method further comprises the step of subtracting the contributions from high frequency components of local motion from the relaxation rates of the heteronuclear bond.

In one embodiment of this type, the relaxation rate of the heteronuclear bond for an isolated selected component in the absence of the rest of the macromolecule is also determined. In a related embodiment, the relaxation rate of the heteronuclear bond of the isolated selected component is measured in the presence and absence of the ligand. In another embodiment, the relaxation rate of the heteronuclear bond for two or more isolated selected components are individually determined in the absence of the rest of the macromolecule. In yet another embodiment the relaxation rate of the heteronuclear bond for all of the isolated selected components are individually determined in the absence of the rest of the macromolecule. Such measurements are preferably performed in the presence and absence of the ligand, particularly when the ligand is believed to bind to the specific isolated component.

In a particular embodiment the heteronuclear bond is a hydrogen—carbon-13 bond. In another embodiment, the heteronuclear bond is a hydrogen—nitrogen-15 bond. In still another embodiment, the heteronuclear bond is a deuterium—carbon-13 bond. In yet another embodiment, the heteronuclear bond is a deuterium—nitrogen-15 bond. In still another embodiment, the heteronuclear bond is a tritium—carbon-13 bond. In yet another embodiment, the heteronuclear bond is a tritium—nitrogen-15 bond.

The methods of the present invention can be performed on any macromolecule that is amenable to NMR spectroscopic analysis. In a preferred embodiment the macromolecule comprises a polymer. In one such embodiment the polymer is a synthetic chemical polymer. In another embodiment the polymer is a biopolymer. In a particular embodiment the biopolymer is a peptide. In another embodiment the biopolymer is a protein (including glycoproteins, lipoproteins and chimeric proteins) such as an enzyme, a transcription factor and/or DNA binding protein, an antibody, a cytokine, a receptor, a ligand for a receptor, or a structural protein. In yet another embodiment the biopolymer is a carbohydrate. In a related embodiment the biopolymer is a lipopolysaccharide. In still another embodiment the biopolymer is a nucleic acid such as a DNA, MRNA, ribosomal RNA or ribozyme. The polymer of the present invention can also be a chimeric polymer formed between two or more biopolymers or a biopolymer and a synthetic chemical polymer. The selected components of the macromolecules of the present invention include protein domains, and prosthetic groups including lipids, lipid polysaccharides as well as small organic molecules such as flavins, porphyrins and the like.

In a particular embodiment of a method of the present invention the macromolecule comprises a peptide component having amide bonds. In this embodiment, the determination of the relaxation rate of the heteronuclear bond contained by the peptide is determined by measuring the $^{15}N$ relaxation rates for the individual amides of the peptide.

In yet another embodiment, the ligand used in the method is a consolidated ligand. One example of one such consolidated ligand is described in the DETAILED DESCRIPTION OF THE INVENTION below.

In one aspect of the method, the macromolecule is a biopolymer that is uniformly labeled with a stable isotope. In one such embodiment the stable isotope is $^{15}N$. In another such embodiment the stable isotope is $^{13}C$. In another aspect of the method, the macromolecule is a biopolymer that is selectively labeled with a stable isotope. In one such embodiment the stable isotope is $^{15}N$. In another such embodiment the stable isotope is $^{13}C$. In a particular embodiment, the biopolymer is a protein that has been segmentally isotopically labeled and then chemically ligated. In a preferred embodiment of this type the isotope is $^{15}N$.

Another aspect of the present invention is a method of identifying an agent that is capable of effecting the orientation of a selected component of a macromolecule in solution. Preferably the macromolecule comprises two or more components. One such embodiment comprises measuring the relaxation rate of a heteronuclear bond contained by a selected component of a macromolecule, in solution, in the presence of a potential agent. The relaxation rate of the heteronuclear bond in the absence of the potential agent is also measured under otherwise the same conditions. The overall hydrodynamic characteristics and the local internuclear vector orientation of the selected components of the macromolecule are derived and it is determined whether there is a change in orientation of the selected components of the macromolecule in the presence of the potential agent. When a change in orientation is determined, a potential agent is identified as an agent that is capable of effecting the orientation of selected components of the macromolecule in solution.

In one embodiment the macromolecule is a protein and the agent identified is a potential agonist or antagonist of the protein. In either case, depending on the identity of the protein, the potential agonist or antagonist can be further characterized by biochemical assays, for example, that measure an activity of the protein. In a particular embodiment of this type, the protein is a multi-domain protein. =P In another embodiment the macromolecule comprises a DNA binding protein bound to its nucleic acid binding site, and the agent identified is a potential agonist or antagonist of the DNA binding protein-nucleic acid interaction. Again, in either case, depending on the identity of the DNA binding protein, the potential agonist or antagonist can be further characterized by biochemical assays, for example, that measure an aspect of the DNA binding protein-nucleic acid interaction, such as an affinity constant.

These and other aspects of the present invention will be better appreciated by reference to the following drawings and Detailed Description.

DETAILED DESCRIPTION OF THE INVENTION

Figure 1:
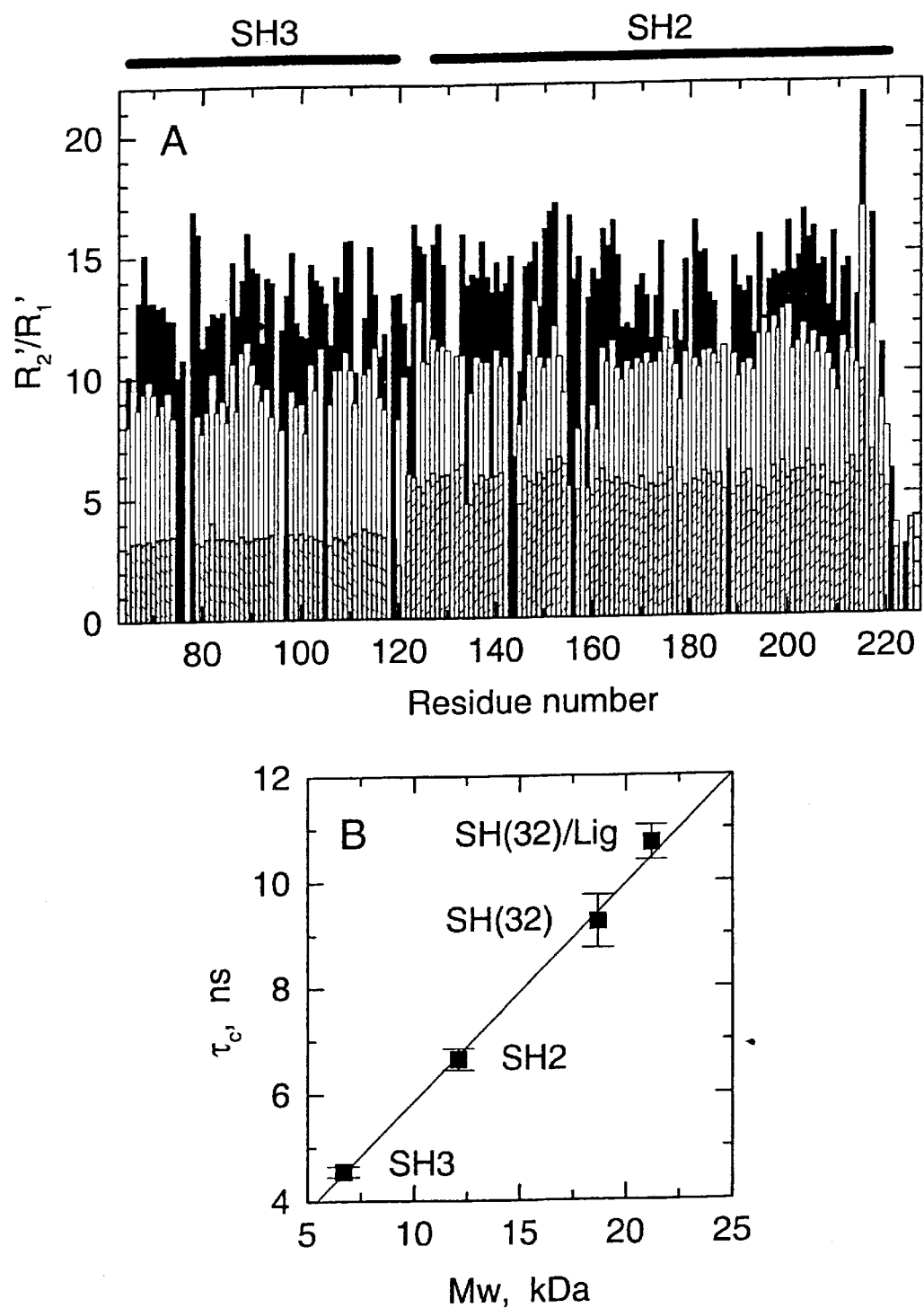
FIG. 1A shows the variation in the experimentally determined backbone $^{15}N$ $R_2'/R_1'$ ratio versus protein sequence. Vertical bars represent the data for the unligated (white), and ligated (black) SH(32), and for the free SH3 and SH2 domains (hatching). Horizontal bars on the top indicate location of the individual domains in the Abl SH(32) dual domain sequence.
FIG. 1B shows the observed molecular weight dependence of the overall rotational correlation time. The two domains SH(32) are not tumbling independently from each other [cf. Hansen et al., *Biochemistry*, 33:15418–15424 (1994)]. Shown are the values of $\tau_c$(ani) (Table 1), derived from the anisotropic analysis as described in the text. The values of $\tau_c$(iso) exhibit similar dependence. The solid line corresponds to a molecular weight dependence $\tau Vc=1.76$ ($\pm 0.20$)$+0.41$($\pm 0.02$) Mw. The observed slope is comparable to 0.33, calculated from the Stokes-Einstein equation for protein density, 0.73 cm$^3$/g and hydration, 0.34 g/g H$_2$O.

The present invention provides a method for determining the orientation of individual components of a macromolecule with respect to the globular molecular coordinate frame of the macromolecule. The orientation can be determined for: (1) the principal axes of the overall rotational diffusion tensor of the macromolecule, or (2) the axes of molecular alignment caused by/due to: (i) an ordered medium, (ii) an electric field, or (iii) a magnetic field.

More particularly, the orientation of the molecular frame is determined for each individual selected component of the macromolecule based on the orientational information for each available group of atoms of the component. The inter-component orientation of the macromolecule is then determined based on the orientation of each individual selected component with respect to the global molecular frame. The orientational information for each available group of atoms of the component is preferably in the form of the internuclear vector orientation derived from either residual dipolar coupling measurements or relaxation data, or a combination of the two. Extraction of the orientational information can be further supplemented by additional information obtained regarding the tertiary structure for any or all of the individual components.

The methods of the present invention can also be combined with conventional methods of structural determination using local constraints (interatomic distances, torsion angles, hydrogen bonds and the like) and/or with the structural refinement determinations for the individual components. The present invention further extends to other cross correlation methods of NMR including methods that involve homonuclear and/or heteronuclear interactions to the analogous method of deriving the orientation of the components of a macromolecule from the local orientation and motion of the components.

Indeed, the range of NMR applications for deciphering the intricacies of macromolecules in solution is considerably enhanced by the hydrodynamic characterization of the macromoleucles by $^{15}N$ relaxation (as disclosed herein for changes in component orientations) in combination with other methods, especially vector orientations studied by residual dipolar coupling [Tjandra and Bax, *Science*, 278:1111–4 (1997) the contents of which are hereby incorporated by reference in its entirety], relaxation-optimized spectroscopy (TROSY) [Pervushin et al., *Proc. Natl. Acad. Sci. U.S.A.*, 94:12366–71 (1997) the contents of which are hereby incorporated by reference in its entirety], and segmental labeling [Xu et al., *Proc. Natl. Acad. Sci. U.S.A.*, 96:388–393 (1999); Yamazaki et al., *J. Am. Chem. Soc.*, 120(22):5591–5592; and Yu, *Proc. Natl. Acad. Sci. U.S.A.*, 96:332–334 (1999) the contents of which each are hereby incorporated by reference in their entireties].

As disclosed in the Example below, the relative orientation has been characterized for the SH2 and SH3 domains in the SH(32) dual domain construct from human Abelson protein-tyrosine kinase (Abl) in solution, either free or in ligated form. The change in domain orientation between unligated and dual ligated domains of the SH(32) segment of Abelson kinase in solution is determined directly, using the orientational dependence of nuclear spin relaxation. A significant change of orientation is thereby directly observed in solution.

Furthermore, the present invention provides an improved, modified calculation of diffusion tensor axes from ratios of relaxation times, and as exemplified below, permits the derivation of the relative orientation of domains in SH(32) in both unligated and ligated states. The analysis of NMR relaxation disclosed herein, and exemplified below, can be extended to directly determine changes of relative orientation of components of any macromolecule in solution, that is amenable to NMR spectroscopic analysis.

A macromolecule of the present invention can be a biopolymer such as a nucleic acid, a protein, or a synthetic chemical polymer such as a polymer of bicyclo [2.2.1] hept-5-ene-exo-2-carboxylic acid N-hydroxysuccinimide ester [Strong and Kiessling, *J. Am. Chem. Soc.* ASAP Article 10.1021/ja990223t S0002-7863(99)00223-1 (1999)]. Components of the macromolecule of the present invention therefore include protein domains, and prosthetic groups including those that are bound to the macromolecule by non-covalent bonds such as a non-covalently bound flavin or a glycolipid such as phosphatidyl inositol.

Thus essentially any $^{15}N$-labeled or $^{13}C$ target molecule can be used in the present invention. Due to the importance of proteins in medicinal chemistry, proteins are a preferred target. The protein can be labeled by any means in the art including by recombinant methodology as discussed below.

The methods disclosed herein can be used to determine heretofore unknown binding sites in proteins and nucleic acids; for rational drug design and/or development of diagnostic agents; or as an aid in the selection of optimized antisense molecules and/or gene therapy reagents. Thus the use of the structural determinations uniquely enabled by the present invention provides a means for identifying agents that can interact with macromolecules (such as small chemical agents e.g., below 1500 daltons in molecular weight) that can act as drugs, diagnostic agents, and the like. Furthermore, such methodology allows the refinement of the structures of such agents to optimize their properties through further defining the basis of the binding of the agent to the macromolecule.

Furthermore, by providing methods of structural characterization, the present invention serves to stimulate the production of polymers incorporating large partially equivalent modomers, in which the overall structural relationships between them can be readily obtained by the methods disclosed herein. Similarly, specific defined chimeric polymers can be more accurately described and more particularly designed using the methods of the invention.

Therefore, if appearing herein, the following terms shall have the definitions set out below:

As used herein the term "component" is used interchangeably with the phrase "component of a macromolecule" and is a constituent of a macromolecule that is associated, preferably but not necessarily by covalent or hydrogen bonding, with the macromolecule. Examples of components of the invention include, protein domains, e.g. Src homology 3, Src homology 1, pleckstrin homology, phosphotyrosine binding domains, [see Ponting, *Nucleic Acid Res.* 27:229–232 (1999); Shultz *Proc. Natl. Acad. Sci.* USA 95:5857–5864 (1998)] protein prosthetic groups such as a heme or a flavin, an iron responsive element (IRE) of mRNA, and a DNA response element such as the interferon-stimulated response element, ISRE. In a particular embodiment a component has a discrete three-dimensional structure that is retained when it is dissociated/severed from the macromolecule.

As used herein a "selected component" is a component of a macromolecule that has been chosen to have its structural characteristics determined. Thus, though a given macromolecule may have many components, the selected components are the ones that are being determined for any given measurement.

As used herein a "macromolecule" is a structured molecule that contains one or more components and has a molecular weight of at least 1500 daltons. Macromolecules of the present invention include biopolymers; a synthetic chemical polymers such as a mannose derivatized polymer of Bicyclo [2.2.1] hept-5-ene-exo-2-carboxylic acid N-hydroxysuccinimide ester; and chimeric polymers as defined below.

As used herein a "biopolymer" is a polymer of monomeric units or derivatives thereof that are naturally found in living cells. Examples of biopolymers are sugar polymers, amino acid polymers including proteins and peptides comprising an unnatural amino acid constituent; and nucleotide polymers including mRNAs, cDNAs, and nucleic acids comprising nucleotide analogs.

As used herein a "chimeric polymer" is a macromolecule which comprises multiple monomeric units (or derivatives thereof) and is not naturally made e.g., as opposed to a macromolecule that is a product of nature. A chimeric polymer can be a polymer comprising a biopolymer or fragment thereof and a synthetic chemical polymer. A particular type of chimeric polymer is a chimeric protein as defined below.

As used herein the terms "chimeric protein" or "chimeric peptide" are used interchangeably with the terms "fusion protein" and "fusion peptide" respectively and are amino acid polymers that do not naturally exist in nature but comprise at least a portion of one or more naturally occurring proteins or peptides.

As used herein the term "consolidated ligand" is a ligand that has at least two binding portions joined together by a linker portion of appropriate length such that the binding portions of the consolidated ligand retain their high affinity and specificity for their respective targets. The linker may have little affinity, or may be modified specially to interact with the intervening, "passive" structure. The consolidated ligands do not necessarily resemble any natural ligand. Thus a consolidated ligand is similar to an affinity reagent, with the modification that the second functionality is a binding element rather than a reactive moiety [see U.S. patent application Ser. No: 08/543,184, Filed Oct. 13,1995, (now abandoned) the disclosure of which is hereby incorporated by reference in its entirety]. In the Example below, the consolidated ligand comprised individual ligands for the SH2 and SH3 domains, NH2-PVpYENVG$_6$> (PPAYAPPPVK-CONH$_2$), where ">"denotes that the C-terminal glycyl residue is linked to the N$^\epsilon$ of lysyl in the second peptide segment [see also Xu et al., *Biochemistry*, 38:3491–97 (1999)].

As used herein the term "Abl" denotes the Abelson protein tyrosine kinase. Abl is a nonreceptor tyrosine kinase originally identified as a viral (v-Abl) product from the transforming gene of Abelson murine leukemia virus [Goff et al. *Cell* 22:777–785 (1980)]. Simple overexpression of Abl in cultured cells does not lead to transformation, but structurally altered forms do. The normal function of Abl may be to modify expression during the cell cycle, possibly mediated by the binding of the retinoblastoma (RB) protein [Wang *TIBS* 19:373–376 (1994)] or in neuralation with other kinases [Koleske, *Neuron* 21:1259–1272 (1998)].

As used herein the term "SH3" denotes the src homology 3 domain whereas the term "SH2" denotes the src homology 2 domain.

As used herein the term "SH(32)" denotes the dual domain of SH3 and SH2.

As used herein the term "relative orientation" means a geometric or analytical expression by which the structural interrelationship between two components of a macromolecule is described.

As used herein a "molecular frame" is a system of coordinates, such as Cartesian or polar coordinates, which are associated with the structure of a macromolecule or component of a macromolecule.

As used herein the term "global molecular coordinate frame" means a system of coordinates, such as Cartesian or polar coordinates, in which the relative orientations of two or more components of a macromolecule exist as separate coordinates within the coordinates of the entire macromolecule.

As used herein the term "inter-component orientation" means the specific relative orientation between two or more components.

As used herein "rotational diffusion axes" has the meaning of describing the coordinate axes in Cartisian frame about which anisotropic rigid-body rotations occur, characterized, by individual rotational diffusion tensors [Woessner, *J. Chem. Phys.*, 37:647–654 (1962)]

As used herein the "orientation of the overall rotational diffusion tensor" is the description of the rotational diffusion tensor in terms of a molecular frame of the angular position of the rotational diffusion axes.

As used herein the "high frequency components of local motion" are those parts of the spectral density detected close to the upper frequencies observed in an NMR experiment, typically the highest resonance frequency observed usually for the detection of $^1$H resonances plus or minus the resonance frequency for the other nucleus. For $^{15}$N, this is: +/−10%; for $^{13}$C, this is: +/−25%.

Relaxation Rate Determinations

Backbone isotopic relaxation parameters, exemplified for simplicity with $^{15}$N for this discussion, comprise the rates of $^{15}$N transverse (R$_2$) and longitudinal (R$_1$) relaxation and the $^5$N{$^1$H} steady-state NOE. The longitudinal relaxation rate (R$_1$) and the transverse relaxation rate (R$_2$) can be measured on any standard high resolution NMR spectrometer. As exemplified below a Bruker DMX600 was used along with the published experimental protocols of Fushman et al.[ *J. Mol. Biol.*, 266:173–194 (1997)]. The sample can approximately contain between 0.5–2.0 mM protein in a buffered solution (though with higher sensitivity spectrometers concentrations of 10 $\mu$M protein or less are feasible) and the spectral analysis can be run at ambient temperatures.

The relaxation rates are optimally modified to subtract contributions from the high-frequency components (P$_{HF}$) of local motion [Fushman and Cowbum, *J. Am. Chem. Soc.*, 120:7109–10 (1998) and Fushman et al., *J. Am. Chem. Soc.*, 120:10947–52 (1998)]. As exemplified below: R$_1$'=R$_1$−6.25 (P$_{HF}$); R$_2$'=R$_2$−5.39 P$_{HF}$, where P$_{HF}$=($\gamma_N$/$\gamma_H$)(1−NOE)R$_1$/5, and Y$_N$ and Y$_H$ are gyromagnetic ratios for $^{15}$N and $_1$H. These equations were obtained from the standard expressions [Abragam, *The Principles of Nuclear Magnetism*, Clarendon Press, Oxford (1961)], under the assumption that the spectral density function scales as J($\omega$) $\omega^{-2}$ at $\omega\approx\omega_H$ [Farrow et al., *J. Biomol.* NMR, 6:153–62 (1995)].

Determination of the overall rotational diffusion tensor. Anisotropic rigid-body rotations of the molecule in general can be characterized by a rotational diffusion tensor D having three principal values, D$_{xx}$, D$_{yy}$, D$_{zz}$. Assuming an axially symmetric overall rotational diffusion tensor (characterized by the principal values D$_\|$=D$_{zz}$ and D$_\perp$=D$_{xx}$=D$_{yy}$) considered here, the dependence of the R$_2$'/R$_1$' ratio on the angle $\theta$ between the NH vector and the unique axis of the tensor can be represented, using the expressions of Woessner [ *J. Chem. Phys.*, 37:647–654 (1962)], as follows:

$$\left(\frac{2R'_2}{R'_1}-1\right)^{-1} = \quad [1]$$

$$\frac{3/4}{1+(\omega_N\tau_1)^2}\left\{1+\frac{(\omega_N\tau_1)^2}{(\omega_N\tau_1)^2+\left(1+\frac{1}{6}\varepsilon\right)^2}\times\frac{\varepsilon\sin^2\theta}{\left[3+2\varepsilon+\left[1+\frac{1}{3}\varepsilon(2-3\sin^2\theta)\right]\right]^2}\left[4+3\varepsilon+\frac{2}{9}\varepsilon^2-\varepsilon\sin^2\theta\left(1+\frac{4+\frac{11}{3}\varepsilon+\frac{19}{18}\varepsilon^2+\frac{5}{54}\varepsilon^3}{(\omega_N\tau_1)^2+\left(1+\frac{2}{3}\varepsilon\right)^2}\right)\right]\right\}$$

where $\varepsilon \equiv D_{\parallel}/D\perp - 1$, $\tau_I^{-1} \equiv 6D\perp$, and $\omega_N$ is the $^{15}$N resonance frequency. An overall rotational correlation time $\tau_c$ can be defined as $\tau_c^{-1} \equiv 6 \text{ tr}(D/3) = 2(D_{\parallel}+2D\perp)$. Equation [1] is exact in the absence of local motion and chemical exchange. This extends the approach to accommodate small, fast tumbling molecules (e.g., $\omega_N\tau_I \sim 1.7$ for the free Abl SH3 domain) and molecules with significant rotational anisotropy. It has previously been demonstrated that possible changes in $R_2'/R_1'$ due to modulation of residue-specific $^{15}$N chemical shift anisotropy tensor are small for the axial ratios determined here, and may be neglected [Fushman and Cowbum, J. Biomol. NMR, 13:139–147; Pushman and Cowburn, J. Am. Chem. Soc., 120:7109–10 (1998) and Fushman et al., J. Am. Chem. Soc., 120:10947–52 (1998)].

Orientation of the principal axes of the diffusion tensor is given by the set of three Euler angles: Φ, θ, and Ψ. Ψ is treated as zero for the assumed axial symmetry. The remaining two angles can be determined, together with $D_{\parallel}$ and $D\perp$, by minimizing the difference between the measured ('exp') and calculated ('calc') values of $f_i = 1/(2R_{2i}'/R_{1i}'-1)$, using the following target function:

$$E = \sum_{i=1}^{N_r}[(f_i^{exp}-f_i^{calc})/\sigma_i]^2$$

where Nr is the total number of residues included in the analysis; and $\sigma_i$ denotes the experimental error in $f_i$ for residue i. $f_i^{calc}$ was obtained using Equation [1], with the θ angle determined as:

$$\theta = \cos^{-1}(\lambda_{ix}\cos\Phi\sin\theta + \lambda_{iy}\sin\Phi\sin\theta + \lambda_{iz}\cos\theta)$$

where $\{\lambda_{ix}, \lambda_{iy}, \lambda_{iz}\}$ are coordinates of a unit vector in the direction of the $NH_i$ bond. To minimize the target function, a search for the optimal values of $D_{\parallel}$ and $D\perp$ can be performed using the simplex algorithm [Press et al., *Numerical Recipes in C*, Cambridge University Press, New York (1992)]; for each set of $D_{\parallel}$, $D\perp$ the optimal values of the Euler angles were obtained by a 1°-step grid search in the $\{\Phi,\theta\}$ space. Confidence limits for the derived parameters can be estimated using the method of constant chi-square boundaries [Press et al., *Numerical Recipes in C*, Cambridge University Press, New York (1992)].

Only those residues belonging to the well-defined secondary structure [Gosser et al., *Structure*, 3:1075–1086 (1995) and Overduin et al., *Cell*, 70:697–704 (1992)] are generally used for the analysis. Residues are generally excluded from the analysis, if they are either being influenced by conformational exchange or participating in slow motion, as indicated by their $R_2'/R_1'$ beyond two standard deviations from the mean.

Segmental Isotopic Labeling of Domains for NMR Studies

Segmental isotopic labeling of components of macromolecules (such as individual domains of proteins) allows selective and/or alternative isotopic labeling of specific components of the macromolecule. Selective labeling of specific domain(s) in a macromolecule allows the NMR analysis of significantly larger macromolecules. Therefore, assignment and high resolution structural determinations of large macromolecules can be performed without requiring the natural spectral simplification that occurs because of molecular symmetry. Furthermore, such fragment (or component) labeling permits the segmental determination of the NMR relaxation rates disclosed herein for macromolecules of essentially any size.

One method for segmental isotopic labeling of proteins can be performed by the trans-splicing approach [Yamazaki et al., *J. Amer. Cem. Soc.* 120:5591–5592 (1998) the contents of which are hereby incorporated by reference in its entirety]. Another preferred approach is "expressed protein ligation" in which synthetic peptides or recombinant proteins can be chemically ligated to the C terminus of peptides or recombinant proteins [Severinov et al., *J. Biol. Chem.* 273:16205–16209 (1998); Muir et al., *Proc. Natl. Acad. Sci. USA* 95:6705–6710 (1998), Xu et al., *Proc. Natl. Acad. Sci.* 96:388–393 (1999) and U.S. Pat. No: 09/191,890 filed Nov. 13,1998, the contents of which each are hereby incorporated by reference in their entireties].

This process employs a recombinant protein α-thioester derivative that can react with an N-terminal cysteine residue in the peptide to form a normal peptide bond. The reactive recombinant protein that contains an α-thioester is prepared in step that is analogous to the natural process of protein splicing [Chong et al., *Gene* 271–281 (1997)]. Suitable protein vectors are commercially available that allow these recombinant proteins to be expressed as, for example, an N-terminal intein-chitin-binding domain fusion protein. The expressed fusion protein can then be purified on chitin beads, immobilized and ligated to a peptide.

Segmental isotopic labeling can be performed in conjunction with the chemical ligation of folded recombinant proteins. Two domains, for example, can be individually prepared with only one being isotopically labeled (e.g., with $^{15}$N) and then the two domains can be ligated together under normal protein-folding conditions to form a standard peptide bond at the ligation junction. In addition, through the chemical ligation method, three or more recombinant protein segments can be regioselectively linked together.

More particularly the chemical ligation segmental isotopic labeling of two protein domains for example, can be performed by expressing portions of one or more proteins having a known nucleic acid sequence by standard recombinant methods. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994). Nucleic acids encoding the selected protein portion (or domain) can be placed into an expression vector (e.g., pGEX2T) and expressed in the presence of an isotope in a prokaryotic host cell, such as *E. coli* DH5-α cells grown in medium containing $^{15}$N-ammonium chloride. The labeled protein can then be isolated and ligated to another peptide or recombinant protein as indicated above and as exemplified below.

Protein-Structure Based Design of Agonists and Antagonists

Once the three-dimensional structure of a macromolecule is determined by the NMR relaxation methods disclosed herein, a potential drug or agent (antagonist or agonist) can be examined either through visual inspection or preferably through the use of computer modeling using a docking program such as GRAM, DOCK, or AUTODOCK [Dunbrack et al., *Folding & Design*, 2:27–42 (1997)]. This procedure can include computer fitting of potential drugs to a particular macromolecule to ascertain how well the shape and the chemical structure of the potential ligand will complement or interfere with the structure of the macromolecule [Bugg et al., *Scientific American*, Dec.:92–98 (1993); West et al., *TIPS*, 16:67–74 (1995)]. Computer programs can also be employed to estimate the attraction, repulsion, and steric hindrance of the potential drug to a binding site, for example. Generally the tighter the fit (e.g., the lower the steric hindrance, and/or the greater the attractive force) the more potent the potential drug will be since these properties are consistent with a tighter binding constant. Furthermore, the more specificity in the design of a potential drug the more likely that the drug will not interfere with related proteins. This will minimize potential side-effects due to unwanted interactions with other proteins.

Initially, a potential drug could be obtained by screening a random peptide library produced by recombinant bacteriophage for example, [Scott and Smith, *Science*, 249:386–390 (1990); Cwirla et al., *Proc. Natl. Acad. Sci.*, 87:6378–6382 (1990); Devlin et al., *Science*, 249:404–406 (1990)]. The effective peptide(s) can be synthesized in large quantities for use in in vivo models and eventually in humans to aid in the fight against diseases when appropriate. It should be emphasized that synthetic peptide production is relatively non-labor intensive, easily manufactured, quality controlled and thus, large quantities of the desired product can be produced quite cheaply. Similar combinations of mass produced synthetic peptides have been used with great success [Patarroyo, *Vaccine*, 10:175–178 (1990)].

A potential drug selected in this manner could be then be systematically modified by computer modeling programs until one or more promising potential drugs are identified. Such analysis has been shown to be effective in the development of HIV protease inhibitors [Lam et al., *Science* 263:380–384 (1994); Wlodawer et al., *Ann. Rev. Biochem.* 62:543–585 (1993); Appelt, *Perspectives in Drug Discovery and Design* 1:23–48 (1993); Erickson, *Perspectives in Drug Discovery and Design* 1:109–128 (1993)].

Alternatively a potential drug and/or agent can be selected from a library of chemicals such as those that can be licensed from most large chemical companies including Merck, GlaxoWelcome, Bristol Meyers Squib, Monsanto/Searle, Eli Lilly, Novartis and Pharmacia UpJohn. A third alternative is to synthesize the potential drug de novo.

The structural analysis disclosed herein in conjunction with computer modeling allows the selection of a finite number of rational chemical modifications, as opposed to the countless number of essentially random chemical modifications that could be made, any of which might lead to a useful drug. Each chemical modification requires additional chemical steps, which while being reasonable for the synthesis of a finite number of compounds, quickly becomes overwhelming if all possible modifications needed to be synthesized. Thus through the use of the NMR relaxation methodology disclosed herein and computer modeling, a large number of these compounds can be rapidly screened on the computer monitor screen, and a few likely candidates can be determined without the laborious synthesis of untold numbers of compounds. As mentioned above, the de novo synthesis of one or even a relatively small group of specific compounds is reasonable in the art of drug design.

Once a potential drug (agonist or antagonist) is identified it can then be tested in any standard assay for the macromolecule depending of course on the macromolecule, including in high throughput assays. When a suitable potential drug is identified, a further NMR structural analysis can optionally be performed. Computer programs that can be used to aid in solving the three-dimensional structure include QUANTA, CHARMM, INSIGHT, SYBYL, MACROMODE, and ICM, MOLMOL, RASMOL, AND GRASP [Kraulis, *J. Appl Crystallogr.* 24:946–950 (1991)].

Using the approach described herein the three-dimensional structures of macromolecules in solution can be solved. Heretofore, the structural detail of macromolecules provided by the methods of the present invention was not available. Indeed, the disclosed methodology permits the determination of potential binding sites on macromolecules which were previously unobtainable, including particular nooks, crannies and surfaces that were not otherwise discernible.

For all of the drug screening assays described herein further refinements to the structure of the drug will generally be necessary and can be made by the successive iterations of any and/or all of the steps provided by the particular drug screening assay, in particular further structural analysis by e.g., $^{15}$N NMR relaxation rate determinations.

These studies are preferably performed in conjunction with biochemical assays which will depend, of course, on the particular macromolecule being investigated. Thus, when the macromolecule is an enzyme, the potential drug can be tested to determine its effect on the corresponding enzymatic activity. Similarly, if the macromolecule is a receptor, the effect of the drug on the ligand-receptor binding can be determined. Such biochemical assays are well known to the skilled artisan.

Thus the drug screening assays of the present invention may use any of a number of means for determining the interaction between a potential drug and a macromolecule. For example, a drug can be initially identified by the methods disclosed herein and then be specifically modified to bind more tightly to a particular macromolecule for example. Other NMR based methodology can then be used in conjunction with these methods [see Shuker et al., *Science* 274:1531–1534 (1996); U.S. Pat. No: 5,698,401, Issued Dec. 16, 1997; U.S. Pat. No. : 5,804,390, Issued Sep. 8, 1998; and U.S. Pat. No. : 5,891,643, Issued Apr. 6, 1999, the contents of which are hereby incorporated by reference herein in their entireties.] However, the order of the methodologies employed will generally be decided on a case by case basis. Thus, the relaxation rate determinations disclosed herein, may be used at any stage of a rational drug design scheme.

In one such embodiment, a library of small chemical compounds is screened to identify a binding partner for a macromolecule. The compounds are individually contacted with a stable isotopically-labeled macromolecule, $^{15}$N for example, and the relaxation rate of the $^{15}$N—$^{1}$H bonds of one or more selected components of the macromolecule are determined. The overall hydrodynamic characteristics and the local internuclear vector orientation of the selected components of the macromolecule are then derived. A compound is then selected if there is a change in orientation of the selected components of the macromolecule in the presence of the compound. An appropriate biochemical assay can be used to further distinguish the selected compounds. Thus, a compound can be further identified as a potential ligand if it binds to the macromolecule and might be selected due to its greater affinity for the macromolecule.

Further refinement of the binding of the compound with the macromolecule can be determined by monitoring the $^{15}$N- or $^{1}$H-amide chemical shift changes in two dimensional $^{15}$N-heteronuclear single-quantum correlation ($^{15}$N-HSQC) spectra upon the addition of the compound to the $^{15}$N-labeled macromolecule for example.

Alternatively, since these spectra can be rapidly obtained, it is feasible to screen a large number of compounds [Shuker et al., Science 274:1531–1534 (1996)] first by $^{15}$N-HSQC and then to refine this determination by the relaxation rate determination methods disclosed herein.

The potential ligand can then be used as a model structure, and analogs to the compound can be obtained (e.g., from the vast chemical libraries that can be licensed for the large chemical companies as cited above, or alternatively through de novo synthesis). The analogs are then screened for their ability to bind the macromolecule to obtain a ligand. An analog of the potential ligand might be chosen as a ligand when it binds to the macromolecule with a higher binding affinity than the potential ligand. In one such embodiment of this type the analogs are screened by monitoring the $^{15}$N- or $^{1}$H-amide chemical shift changes in $^{15}$N-HSQC spectra upon the addition of the analog to the $^{15}$N-labeled macromolecule as described above. In a preferred embodiment the analogs selected after this assay are further screened by the relaxation rate determination of the present invention.

In another embodiment, compounds are screened for binding to two nearby sites on an macromolecule. In this case, a compound that binds a first site of the macromolecule does not bind a second nearby site. Binding to the second site can be determined by monitoring changes in a different set of amide chemical shifts in either the original screen or a second screen conducted in the presence of a ligand (or potential ligand) for the first site. From an analysis of the chemical shift changes the approximate location of a potential ligand for the second site is identified. Optimization of the second ligand for binding to the site is then carried out by screening structurally related compounds (e.g., analogs as described above). When ligands for the first site and the second site are identified, their location and orientation in the ternary complex can be determined experimentally either by standard NMR spectroscopy, an/or X-ray crystallography and/or preferably by the NMR relaxation rate methods disclosed herein. On the basis of this structural information, a linked compound, e.g., a consolidated ligand, is synthesized in which the ligand for the first site and the ligand for the second site are linked. In a preferred embodiment of this type the two ligands are covalently linked in a consolidated ligand. This consolidated ligand can be tested to determine if it has a higher binding affinity for the macromolecule than either of the two individual ligands. A consolidated ligand is selected as a ligand when it has a higher binding affinity for the macromolecule than either of the two ligand. In a preferred embodiment the affinity of the consolidated ligand with the macromolecule is determined monitoring the NMR relaxation as described herein and/or the $^{15}$N- or $^{1}$H-amide chemical shift changes by $^{15}$N-HSQC spectra upon the addition of the consolidated ligand to the $^{15}$N-labeled macromolecule as described above.

Larger consolidated ligands can be constructed in an analogous manner, e.g., linking three ligands which bind to three nearby sites on the macromolecule to form a multi-linked consolidated ligand that has an even higher affinity for the macromolecule than linked compound.

In still another aspect of the present invention, solution and/or crystal structures of individual domains of a multi-domain protein can first be determined and then used as high resolution structures for the procedure of defining relative domain orientation disclosed herein for the intact multidomain protein. The resulting structural determination for the multidomain protein can then be used as to identify new binding sites arising from the close interactions of the constituent domains. The binding sites that are identified can in turn be used as a target for rational drug design in order to identify bioactive compounds useful as therapeutic agents (e.g. drugs) or alternatively as diagnostic reagents of the state of the protein. Such changes in relative orientation of protein domains might occur as the result of postsynthetic modifications, e.g., protein phosphorylation in which a tyrosine, serine, histidine, or threonine residue is phosphorylated. An example of the effect of protein phosphorylation is the proposed structural change due to the phosphorylation of protein tyrosine kinases of the Src class which also modifies their enzymatic activity [Sicheri and Kuriyan, *Curr, Op, Str. Biol.* 7: 777–785 (1997)].

The methods provided by the present invention may also be used in designing new macromolecules. Thus based on analysis of the relative orientations of the components by the methods disclosed herein novel macromolecules can be constructed through either total synthesis or by ligation of expressed proteins of chimeras, whose individual component structures can be precisely modified by site specific mutation (or site directed substitution), or residue or component substitution by total synthesis. For example, the relative orientation of rigid analogs of the AOP component might be analyzed in a series of homologues of AOP-RANTES, a totally synthetic anti-HIV agent [e.g. Wilken et al., 6:43–51 *Chem. Biol.* (1999)].

The present invention further provides a method of using the relaxation rate determinations disclosed herein with a high resolution crystal structure of a multidomain protein to define the likely orientation of heteronuclear bonds in component domains. In this case relaxation rate determination would be used to define the actual, in solution, component orientations. This is likely to differ from the crystal structure form, and thereby provide unique information for rational drug design as outlined above. For example, the domain orientations in SH(32) in solution described below differ considerably from that previously determined in a crystal. [Nam et al., *Structure* 4:1105–1114 (1996)].

The present invention may be better understood by reference to the following non-limiting Example, which is provided as exemplary of the invention. The following example is presented in order to more fully illustrate the preferred embodiments of the invention. It should in no way be construed, however, as limiting the broad scope of the invention.

EXAMPLE

Direct Determination of Changes of Interdomain Orientation on Ligation: Use of the Orientational Dependence of $^{15}$N NMR Relaxation in Abl SH (32)

Introduction

The human Abelson protein-tyrosine kinase (Abl) is protooncogenic for chronic myelogenous leukemia, caused by chromosomal translocation, leading to disordering of the normal down-regulated kinase [Deiningen and Goldman, *Curr. Opin. Hematol.*, 5:302–8 (1998)]. As indicated above, Abl also has both an SH2 domain and an SH3 domain. Therefore, Abl was selected as an archetypal system for the relative reorientation of the individual domains in multidomain proteins. In Abl SH(32), the two domains are separated by a six residue native-sequence linker.

Proteins that contain SH2 and SH3 domains fall into two broad classes: those with catalytic functions and those without. Enzymes that contain these domains include cytoplasmic tyrosine kinases (e.g., Src, Abl, Lck), phosphotyrosine phosphatases, phospholipase C gamma (PLC gamma), ras GTPase-activating protein (GAP) and nucleotide exchange factors [Koch et al., *Science*: 252:668–674 (1991)]. The SH2 and SH3 domains in these proteins serve to modulate enzyme activity, or to target the enzymes to certain cellular locations. The second class of SH2 and SH3 containing proteins do not exhibit enzymatic activity. Some of these "adapter" proteins bind to enzymes that contain the appropriate targeting sequences (i.e., phosphorylated tyrosines or specific proline-rich sequences) and modulate their activity. For example, the p85 subunit of phosphatidyl inositol 3-kinase (PI3K) contains SH3 and SH2 domains, but has no catalytic activity. Instead, it serves to potentiate the activity of the kinase subunit, and is also important in localizing this enzyme to the vicinity of activated receptors [Cantley et al., *Cell* 64:281–302 (1991); Panay et al. *EMBO* 11:461–472 (1992); Carpenter et al. *J. Biol. Chem.* 268:9478–9483 (1993); Shoelson et al. *EMBO* 12:795–802 (1993)]. Overduin et al. [*Cell* 70:697–704 (1992)] determined the structure of the abl SH2 product, a protein of 109 residues and 12.1 kDa, by multidimensional nuclear magnetic resonance spectroscopy. It is a compact spherical domain with a pair of three-stranded antiparallel beta sheets and a C-terminal alpha helix enclosing the hydrophobic core. Three arginines project from a short N-terminal alpha helix and one beta sheet into the putative phosphotyrosine binding site, which lies on a face distal from the termini. Comparison with other SH2 sequences supports a common global fold and mode of phosphotyrosine binding for this family.

The crystal structure of unligated Abl SH(32) [Nam et al., *Structure*, 4:1105–1114 (1996)] shows significant intramolecular contacts between the two domains, in particular, at the BC-loop of SH2, which is involved in phosphotyrosine binding. On the other hand, solution studies [Gosser et al., *Structure*, 3:1075–1086 (1995); Xu et al., *Proc. Natl. Acad. Sci.* U.S.A., 96:388–393 (1999); and Xu et al., *Biochemistry*, 38:3491–97 (1999)] indicate that there are few interdomain contacts in solution, and that the binding sites are completely independent. This apparent controversy illustrates the difficulties of understanding these kinds of systems fully. In addition, the NOESY NMR spectra of Abl SH(32) provide a negligible amount of information on possible contacts between the domains, certainly not sufficient to determine their relative orientation in the Abl SH(32). Therefore, an alternative approach is required to obtain the critical information regarding the change in the dual domain structure of a protein in the free state relative to the structure when at least one of the domains is complexed with a ligand.

As a model of possible ligation for multidomain proteins, the 'consolidated ligands', incorporating individual ligands for SH3 and SH2 domains tethered by an oligoglycyl linker, have been shown to bind with enhanced affinity to SH(32) [Xu et al., *Biochemistry*, 38:3491–97 (1999) Cowbum et al., *J. Biol. Chem.*, 270:26738–26741 (1995), and see U.S. patent application No: 08/543,184, (now abandoned) Filed Oct. 13, 1995, the contents of which each are hereby incorporated by reference in their entireties]. Such consolidated ligands can be used to turn on and off the relative motion of the domains, allowing the study of the domain-domain interaction, as well as the effect of a ligand on the multiple domain motion.

Materials And Methods

Experimental procedures. Protein and ligand preparation, and NMR structure determination of the individual domains have been reported previously [Gosser et al., *Structure*, 3:1075–1086 (1995) and Overduin et al., *Cell*, 70:697–704 (1992)]. NMR signal assignment for both free and complexed states of Abl SH(32) has been reported in Xu et al.,[*J. Biomol. NMR*, (1999); deposited in Biomagresbank Accession Nos: 4251, 4252 (November 1998) www.bmrb.wisc.edu]. The backbone $^{15}$N relaxation parameters, comprising the rates of $^{15}$N transverse ($R_2$) and longitudinal ($R_1$) relaxation and the $^{15}$N{$^1$H} steady-state NOE, were measured on a Bruker DMX600 using previously described experimental protocols [Fushman et al., *J. Mol. Biol.* 266:173–194 (1997)]. Protein concentration in phosphate-buffered saline was ~1.5 mM for the SH3, 3 mM for SH2, and 500 µM for the free and 600 µM for the ligated SH(32); pH was adjusted to pH 7.2, the sample temperature was 31° C. The consolidated ligand comprised individual ligands for the SH2 and SH3 domains, NH2–PVpYENVG$_6$>(PPAYAPPPVK–CONH$_2$), where ">" denotes that the C-terminal glycyl residue is linked to the N$^\epsilon$ of lysyl in the second peptide segment [Xu et al., *Biochemistry*, 38:3491–97 (1999)].

Data analysis. The relaxation rates were modified to subtract contributions from the high-frequency components ($P_{HF}$) of local motion [Fushman and Cowburn, *J. Am. Chem. Soc.*, 120:7109–10 (1998) and Fushman et al., *J. Am. Chem. Soc.*, 120:10947–52 (1998)], as follows: $R_1' = R_1 - 6.25(P_{HF})$; $R_2' = R_2 - 5.39\, P_{HF}$, where $P_{HF} = (\gamma_N/\gamma_H)(1-\text{NOE})R_1'/5$, and $\gamma_N$ and $\gamma_H$ are gyromagnetic ratios for $^{15}$N and $^1$H. These equations were obtained from the standard expressions [Abragam, *The Principles of Nuclear Magnetism*, Clarendon Press, Oxford (1961)], under the assumption that the spectral density function scales as $J(\omega)\, \omega^{-2}$ at $\omega \approx \omega_H$ [Farrow et al., *J. Biomol. NMR*, 6:153–62 (1995)]. Thus, "$R_1$" is the longitudinal relaxation rate; and "$R_2$" is the transverse relaxation rate.

Determination of the overall rotational diffusion tensor. Anisotropic rigid-body rotations of the molecule in general can be characterized by a rotational diffusion tensor D having three principal values, $D_{xx}$, $D_{yy}$, $D_{zz}$. Assuming an axially symmetric overall rotational diffusion tensor (characterized by the principal values $D_\| = D_{zz}$ and $D_\perp D_{xx} = D_{yy}$) considered here, the dependence of the $R_2'/R_1'$ ratio on the angle θ between the NH vector and the unique axis of the tensor can be represented, using the expressions of Woessner [*J. Chem. Phys.*, 37:647–654 (1962)], as follows:

$$\left(\frac{2R_2'}{R_1'} - 1\right)^{-1} = \quad [1]$$

$$\frac{3/4}{1+(\omega_N\tau_1)^2}\left\{1 + \frac{(\omega_N\tau_1)^2}{(\omega_N\tau_1)^2 + \left(1+\frac{1}{6}\varepsilon\right)^2} \times \frac{\varepsilon \sin^2\theta}{3 + 2\varepsilon + \left[1+\frac{1}{3}\varepsilon(2-3\sin^2\theta)\right]^2}\left[4 + 3\varepsilon + \frac{2}{9}\varepsilon^2 - \varepsilon\sin^2\theta\left(1 + \frac{4+\frac{11}{3}\varepsilon+\frac{19}{18}\varepsilon^2+\frac{5}{54}\varepsilon^3}{(\omega_N\tau_1)^2+\left(1+\frac{2}{3}\varepsilon\right)^2}\right)\right]\right\}$$

where $\varepsilon \equiv D_\|/D_\perp - 1$, $\tau_1^{-1} \equiv 6D_\perp$, and $\omega_N$ is the $^{15}$N resonance frequency. An overall rotational correlation time $\tau_c$ can be defined as $\tau_c^{-1} \equiv 6\text{tr}(\underline{D}/3) = 2(D_\| + 2D_\perp)$. Equation [1] is exact in the absence of local motion and chemical exchange. It provides a good approximation for the protein core residues, characterized by restricted mobility in the protein backbone, and is more general than those used previously [Lee et al., *J. Biomol. NMR*, 9:287–98 (1997) and Copie et al., *J. Mol. Biol.*, 277:663–682 (1998)], which are valid only for small anisotropies ($\varepsilon < 1$) and for $\omega_N^{96} \tau_1 \gg 1$. This then extends the approach to accommodate small, fast tumbling molecules (e.g., $\omega_N\tau_1 \sim 1.7$ for the free Abl SH3 domain) and molecules with significant rotational anisotropy. It has previously been demonstrated that possible changes in $R_2'/R_1'$ due to modulation of residue-specific $^{15}$N chemical shift anisotropy tensor are small for the axial ratios determined here, and may be neglected [Fushman and Cowburn, *J. Biomol. NMR*, 13:139–147; Fushman and Cowburn, *J. Am. Chem. Soc.*, 120:7109–10 (1998) and Fushman et al., *J. Am. Chem. Soc.*, 120:10947–52 (1998)].

Orientation of the principal axes of the diffusion tensor is given by the set of three Euler angles: Φ, θ, and Ψ. Ψ is treated as zero for the assumed axial symmetry. The remaining two angles were determined, together with $D_\|$ and $D_\perp$, by minimizing the difference between the measured ('exp') and calculated ('calc') values of $f_i = 1/(2R_2'/R_{1i}' - 1)$, using the following target function:

$$E = \sum_{i=1}^{N_r} [(f_i^{\text{exp}} - f_i^{\text{calc}})/\sigma_i]^2$$

where $N_r$ is the total number of residues included in the analysis; and $\sigma_i$ denotes the experimental error in $f_i$ for residue i. $f_i^{\text{calc}}$ was obtained using Equation [1], with the θ angle determined as:

θ = cos$^{-1}$($\lambda_{ix}$ cosΦ sinθ + $\lambda_{iy}$ sinΦ sin θ + $\lambda_{iz}$ cosθ)

where {$\lambda_{ix}, \lambda_{iy}, \lambda_{iz}$} are coordinates of a unit vector in the direction of the NH$_i$ bond. To minimize the target function, as search for the optimal values of $D_\|$ and $D_\perp$ was performed using the simplex algorithm [Press et al, *Numerical Recipes in C*, Cambridge University Press, NY (1992)]; for each set of $D_\|$, $D_\perp$, the optimal values of the Euler angles were obtained by a 1°-step grid search in the {Φ,θ} space. Confidence limits for the derived parameters were estimated using the method of constant chi-square boundaries [Press et al., *Numerical Recipes in C*, Cambridge University Press, NY (1992)].

Only those residues belonging to the well-defined secondary structure [Gosser et al., *Structure*, 3:1075–1086 (1995) and Overduin et al., *Cell*, 70:697–704 (1992)] were used for the analysis. Of the core residues in the SH2 domain, 61, 59, and 59 residues were effectively resolved in the free SH2, in the unligated, and in ligated SH(32), respectively. The corresponding numbers for SH3 are 30, 29, and 30. The following residues were excluded from the analysis, as either being influenced by conformational exchange or participating in slow motion, as indicated by their $R_2'/R_1'$ values beyond two standard deviations from the mean. These were S134, R135, Q160, N193, T204, and A217 in the free SH2, Q160, R161, and S148 in the unligated, and R161, T178 in the ligated SH(32). Excluded from the analysis for the SH3 domain were I82 in the free SH3, L80, R89 in the unligated, and K87, R89, and W99 in the ligated SH(32).

Protein coordinates. The following protein atom coordinate sets were used for the analysis: 1abq.pdb (single Abl SH3 domain), 1abo.pdb (Abl SH3 complexed with ligand), 1abl.pdb (single Abl SH2 domain), and 2abl.pdb (Abl SH(32)). Amide hydrogen atoms were added to crystal structures' coordinates, as necessary, using Insight II (MSI). All these coordinate sets yielded similar results (See below).

Results And Discussion

The ratio, $R_2'/R_1'$, of the experimentally determined $^{15}N$ relaxation rates for individual amides in the proteins under investigation is shown in FIG. 1. For those residues with restricted local dynamics, both the overall hydrodynamic characteristics of the molecule and the local inter-nuclear vector orientation can be directly derived from the observed values of the $R_2'/R_1'$, ratio, using Equation [1]. These measurements were obtained for the free and ligated SH(32) dual domain construct, and for the individual domains, as controls. Variations in the individual values of $R_2'/R_1'$ along the protein backbone principally reflect different orientation of the individual NH bonds with respect to the rotational diffusion frame. The observed patterns of $R_2'/R_1'$, vs. residue number (FIG. 1A), reflecting changes in orientation of the rotational diffusion tensor, differ significantly between free and ligated states.

The apparent correlation time, $\tau_{app}$, can be obtained from $R_2'/R_1'$ for each amide group without any reference to protein structure [Fushman et al., *J. Biomol. NMR* 4:61–78. (1994)]:

$$\tau app=(2\omega_N)^{-1}\sqrt{6R_2'/R_1'-7}$$

In the case of isotropic rotational diffusion ($D_\parallel = D\perp$), $\tau_{app}$ coincides with the overall (isotropic) correlation time $\tau_c$. The observed average levels of apparent isotropic $\tau_{app}$ [column $\tau_c$(iso), Table 1] for the free SH3, SH2, SH(32) (9.27±0.07 ns), and for the SH(32)/ligand complex (10.79+0.11 ns) increase linearly with the molecular weight, 6.7, 12.1, 18.7, and 21.2 kDa, respectively, of these proteins (see also FIG. 1B). Higher values of the apparent rotational correlation time for the individual domains in the dual domain construct compared to the free domains in solution, suggest the presence of restricted rotational diffusion of the domains imposed by the linker. Differences in the average levels of $\tau_{app}$ in the SH3 and SH2-parts of the free dual domain construct, although small, indicate some degree of interdomain flexibility in SH(32). No significant difference was observed between the average $\tau_{app}$ values for the two domains in the SH(32)/ligand complex, consistent with restriction in the interdomain flexibility expected upon binding of the consolidated ligand. This relation between the overall tumbling times for individual domains in a dual domain protein is different from that reported in [Hansen et al, *Biochemistry*, 33:15418–15424 (1994)], where large differences between the correlation times of the individual domains in a two-domain protein were observed, consistent with those of independent beads on a string. The rotational correlation times of the SH2 and SH3 domains in SHE(32) observed here indicate the presence of certain orientational constraints between the two domains, and, therefore, confirm the proposed method of characterization of interdomain orientation using relaxation data.

Figure 2:
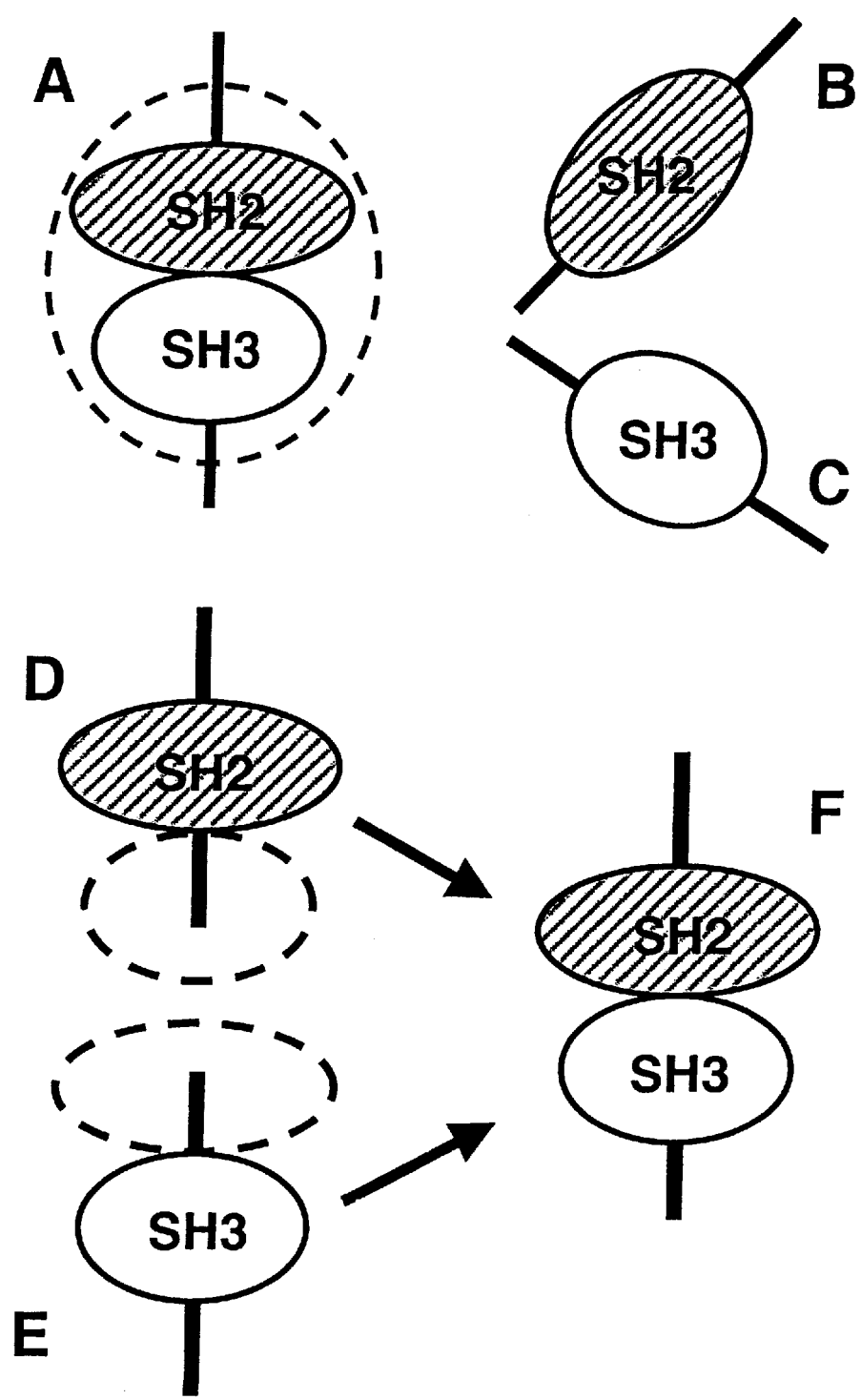
FIGS. 2A–2F show a schematic representation of the proposed method of determination of relative orientation of the domains in a dual domain protein. The overall rotational diffusion of individual domains in a multidomain protein or protein complex (FIG. 2A) is characterized by the common diffusion tensor; the orientation of the principal axes of this tensor may differ from those for the individual domains in a free state (FIGS. 2B and 2C). The proposed method consists of, first, determination of the diffusion tensors for each of the domains in a dual domain construct separately (FIGS. D and 2E), and, second, alignment of the rotational diffusion axes of the individual domains (FIG. 2F), thereby determining a proper relative orientation of the domains.

To quantify these observations, the average orientation of the overall rotational diffusion tensor was determined for each of the domains, using the measured $R_2'/R_1'$ ratio. The approach, illustrated in FIG. 2, assumes that the backbone tertiary structure of the individual domains is substantially preserved in the dual domain. The amide $^1H$ and $^{15}N$ chemical shifts in the individual domains and in SH(32) are nearly identical [Gosser et al., *Structure*, 3:1075–1086 (1995)]. For example, only 6% of the amide groups in the SH2 and 6% in the SH3 domain exhibit a total chemical shift difference between the free state and the dual domain construct of more than 30 Hz at 600 MHz. A similar picture is observed for the ligated SH(32): only 10% of amide signals are shifted by more than 30 Hz in the SH(32)/Ligand complex compared to the free SH2 bound to the ligand. Changes in orientation of amides between free and ligated SH3 in crystal state are very small [Musacchio et al., *Nature Structural Biology*, 1:546–551 (1994)]; most changes are located in the RT-Src loop. Although no structural data are currently available on the Abl SH2/ligand complex, a comparison of the crystal structures of the other SH2 domains, from Src [Waksman et al., *Cell*, 72:779–90 (1993)] and from SYP tyrosine phosphatase [Lee et al., *Structure*, 2:423–438 (1994)], in the free form and bound to various phosphotyrosine containing peptides indicate only minor changes in the structure of the protein core. No significant changes in the result were observed when those residues in both domains involved in ligand binding were excluded from the analysis for the ligated SH(32). While an approximation, the assumption that the axes can be determined from the orientations of the core of the Abl SH2 and SH3 domains is found to be entirely reasonable. The treatment used here derives a time-averaged set of anisotropic axes, and the relative orientational dependence derived is not dependent on interdomain scalar effects, such as NOE's. This analysis therefore, fundamentally extends that of Tjandra et al. [*Nat. Struct. Biol.*, 4:443–9 (1997)] which assumed a time-independent, fixed relationship between domains.

Figure 4:
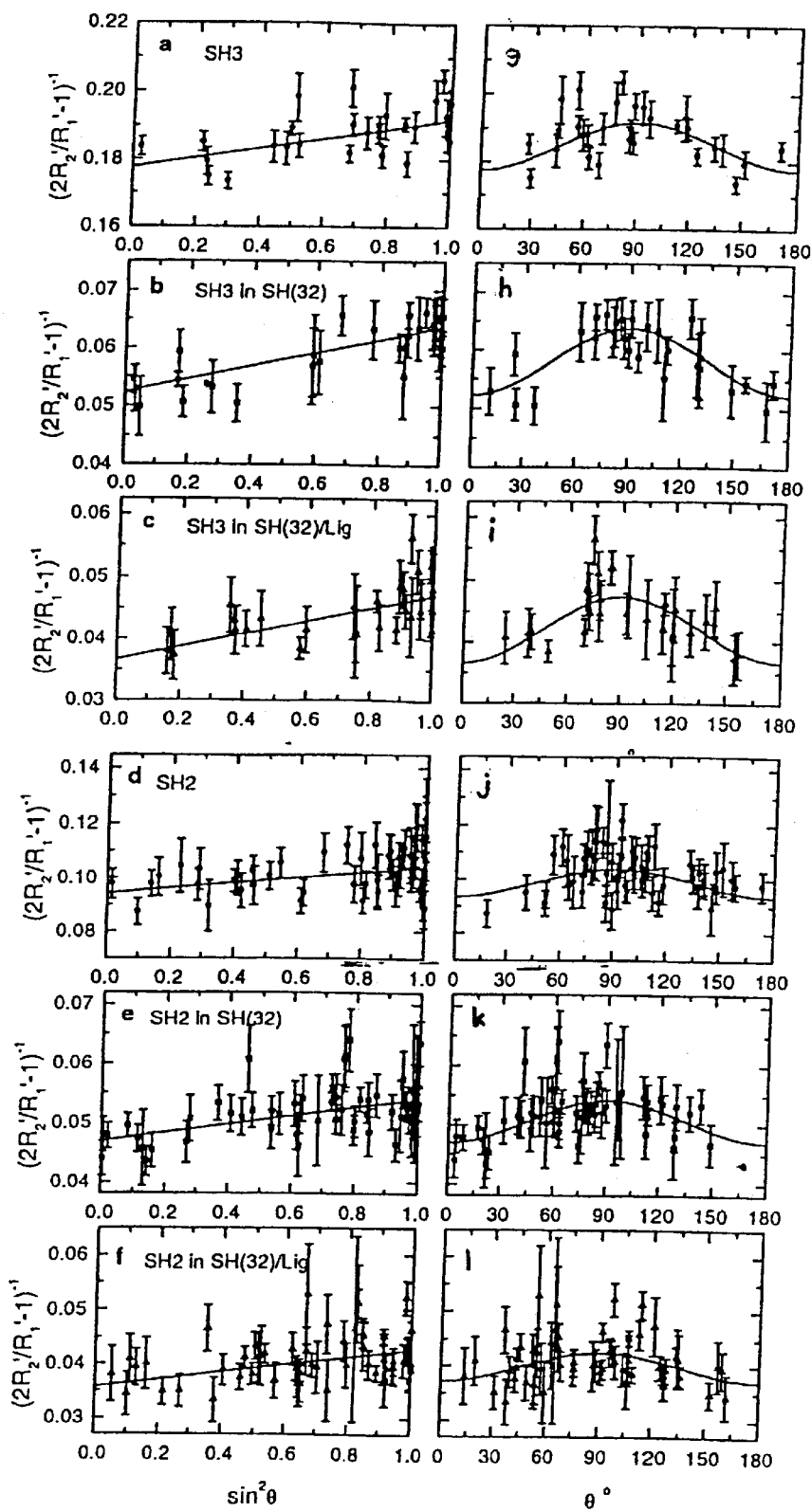
FIGS. 4a–4f show the resulting sin$^2\theta$-dependence and FIGS. 4g–4l show the resulting $\theta$-dependence of the R$_2$'/R$_1$' data for the SH3 and SH2 domains, respectively, in the unligated single domain form (FIGS. 4a, 4g, 4d, and 4j), and in the unligated (FIGS. 4b 4h, 4e, and 4k) and ligated (FIGS. 4c, 4i, 4f, and 4l) SH(32). The fitting curves are represented by solid lines.
Figure 5:
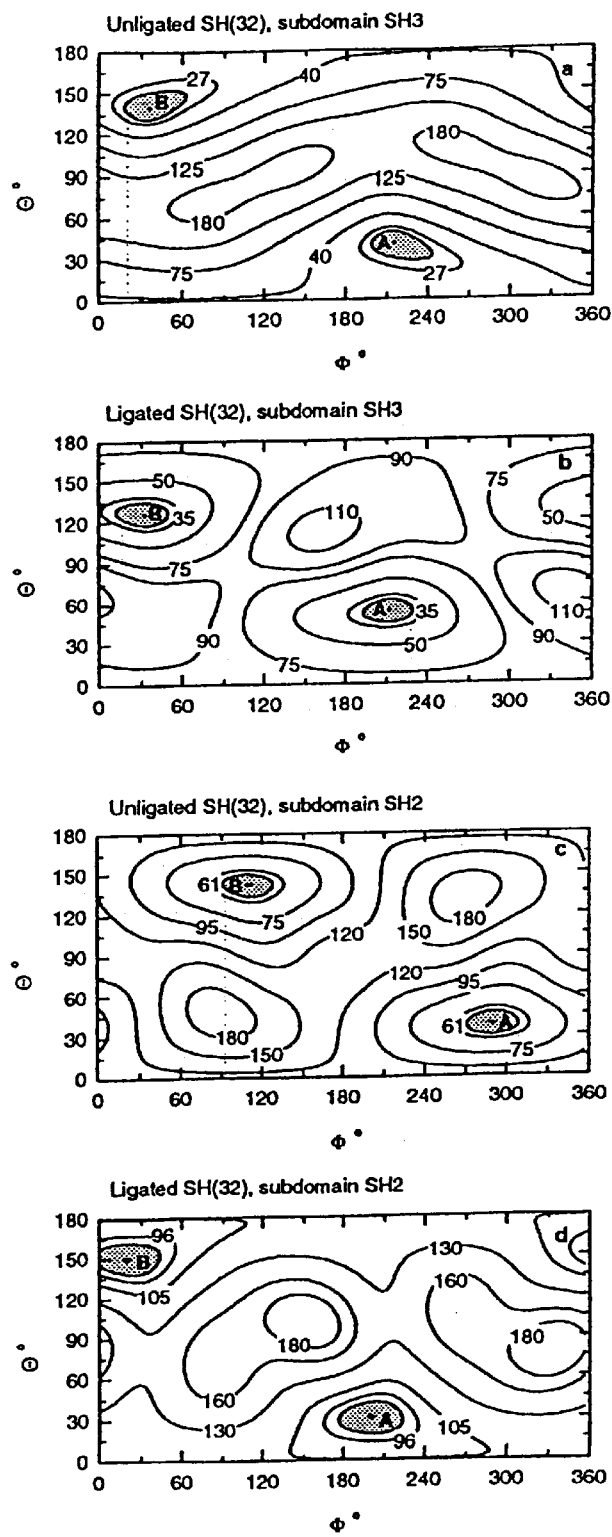
FIGS. 5a–5d show the contour map of the optimized target function, E, in angular coordinates $\Phi$ and $\Theta$ for the SH3 (FIGS. 5a, and 5b) and SH2 (FIGS. 5c and 5d) domains, in the unligated and ligated SH(32). The minima are indicated by letters A and B; the shaded areas around the minima correspond to 68.3% confidence levels for the joint distribution of $\Phi$ and $\Theta$. Numbers near the contour lines indicate the values of E. Two sets of {$\Phi$ and $\Theta$}-angles, indicated on the map as A and B, are consistent with the data, because of the axial degeneracy of the analysis. These two sets are equivalent, related by the symmetry transformations: $\Phi_A=\Phi_B+180°$, $\Theta_b=180°-\Theta_A$, and correspond to the opposite orientations of the Z-axis of the rotational diffusion tensor. In the case of dual domain construct, the selection of proper pairs from the {$\Phi$, $\Theta$} angles determined for the individual domains can be done based on restrictions imposed by their chemical linkage. The selected pairings, as shown in FIGS. 2c and 2d, are A$_{SH3}$—B$_{SH2}$ and B$_{SH3}$—A$_{SH2}$.

Shown in Table 1 are results obtained using the following atom coordinates for the single protein domains: 1abo.pdb (for SH3) and 1abl.pdb (for SH2). A more complete report on the results using these and other available structures is in Table 2, below and FIGS. 4 and 5.

TABLE 1

Characteristics of the overall rotational diffusion of Abl Src homology construct derived from the $^{15}$N relaxation data.

| Protein | $D_\parallel/D_\perp$ | $\Phi^\circ$ | $\Theta^\circ$ | E/N† | P‡(%) | $\tau_c$(ani)§(ns) | $\tau_c$(iso)¶(ns) |
|---|---|---|---|---|---|---|---|
| SH(32) unligated, domain SH3 | 1.24(0.05) | 216(21) | 40(10) | 0.98 | 0.0003 | 8.89(0.20) | 8.85(0.11) |
| SH(32) ligated, domain SH3 | 1.30(0.09) | 212(19) | 54(9) | 1.26 | 0.59 | 10.51(0.51) | 10.61(0.14) |
| SH3 | 1.10(0.05) | 290(18) | 60(12) | 3.11 | 1.49 | 4.55(0.10) | 4.50(0.04) |
| SH(32) unligated, domain SH2 | 1.16(0.04) | 290(19) | 38(9) | 1.08 | 0.002 | 9.61(0.20) | 9.49(0.07) |
| SH(32) ligated, domain SH2 | 1.20(0.08) | 200(26) | 30(13) | 1.66 | 1.7 | 10.95(0.42) | 10.89(0.14) |
| SH2 | 1.12(0.06) | 197(17) | 88(21) | 1.26 | 3.9 | 6.65(0.20) | 6.52(0.05) |

† The target function E shown here was normalized by the number of degrees of freedom, which in this analysis is $N = N_r - N_{par}$, where $N_r$ is the number of residues used, and $N_{par} = 4$ representing the number of fitting parameters: $\tau_1$, $D_\parallel/D_\perp$, $\Theta$, and $\Phi$.
‡ P is the percentile probability that the observed improvement in fit using the anisotropic rotational diffusion model compared to the isotropic one could have occurred by chance [Draper and Smith, Applied Regression Analysis, John Wiley & Sons, New York].
§ $t_c$(ani) was calculated as $\tau_c = 3\tau_1/(D_\parallel/D_\perp + 2)$, where $\tau_1$ and $D_\parallel/D_\perp$ were derived from orientational dependence of $R_2'/R_1'$ for the core residues.
¶ $\tau_c$(iso) was determined as an averaged apparent individual correlation time, $\tau_{app}$, for the core residues.

Numbers in parentheses indicate standard errors in the derived values.

TABLE 2

Detailed characteristics of the overall rotational diffusion of the proteins studied here, derived from the present analysis of $^{15}$N relaxation data.

| Protein | Str.& | $\tau_1$(ns) | $D_\parallel/D_\perp$ | $\Phi^\circ$ | $\Theta^\circ$ | E/N† | Nr‡ | F§ | P‖(%) | $\tau_c$(ani) (ns) | $\tau_c$(iso) (ns) |
|---|---|---|---|---|---|---|---|---|---|---|---|
| SH(32) unligated, domain SH3, | SH3-I | 9.58 (0.16) | 1.24 (0.05) | 216 (21) | 40 (10) | 0.98 | 27 | 18.03 | 0.0003 | 8.89 (0.20) | 8.98 |
| | SH3-II | 9.55 (0.14) | 1.23 (0.04) | 210 (19) | 38 (12) | 0.91 | 27 | 19.90 | 0.0001 | 8.89 (0.18) | 8.98 |
| | SH32a | 9.45 (0.14) | 1.21 (0.04) | 228 (30) | 29 (14) | 1.00 | 27 | 17.38 | 0.0004 | 8.84 (0.18) | 8.98 |
| SH(32) ligated, domain SH3, | S113-I | 11.57 (0.44) | 1.30 (0.09) | 212 (18) | 54 (8) | 1.26 | 27 | 5.39 | 0.59 | 10.51 (0.51) | 10.47 |
| | SH3-II | 11.27 (0.37) | 1.23 (0.09) | 178 (30) | 46 (11) | 1.36 | 27 | 4.41 | 1.36 | 10.45 (0.45) | 10.47 |
| | SH32a | 11.57 (0.41) | 1.31 (0.09) | 208 (16) | 54 (8) | 1.19 | 27 | 6.12 | 0.32 | 10.48 (47) | 10.47 |
| SH3 | SH3-I | 4.70 (0.07) | 1.10 (0.05) | 290 (17) | 60 (12) | 3.11 | 29 | 4.2 | 1.49 | 4.54 (0.10) | 4.55 |
| | SH3-II | 4.67 (0.07) | 1.09 (0.04) | 297 (22) | 63 (160 | 3.40 | 29 | 3.18 | 4.14 | 4.54 (0.09) | 4.55 |
| | SH32a | 4.7 (0.07) | 1.09 (0.04) | 299 (21) | 60 (15) | 3.40 | 29 | 3.19 | 4.10 | 4.53 (0.09) | 4.55 |
| SH(32) unligated, domain SH2 | SH2 | 10.11 (0.16) | 1.16 (0.04) | 290 (20) | 38 (9) | 1.08 | 56 | 9.95 | 0.003 | 9.61 (0.20) | 9.64 |
| | SH32b | 10.10 (0.13) | 1.16 (0.04) | 312 (17) | 42 (8) | 0.90 | 55 | 13.8 | 0.0001 | 9.60 (0.17) | 9.64 |
| SH(32) ligated, domain SH2 | SH2 | 11.59 (0.34) | 1.18 (0.08) | 200 (26) | 30 (13) | 1.66 | 57 | 3.70 | 1.7 | 10.95 (0.42) | 10.89 |
| | SH32b | 11.46 (0.31) | 1.14 (0.07) | 238 (66) | 18 (40) | 1.52 | 56 | 3.01 | 3.8 | 10.95 (0.39) | 10.91 |
| SH2 | SH2 | 6.91 (0.15) | 1.12 (0.06) | 197 (18) | 88 (22) | 1.26 | 55 | 2.99 | 3.9 | 6.65 (0.20) | 6.64 |
| | SH32b | 7.02 (0.16) | 1.17 (0.06) | 188 (13) | 70 (12) | 1.15 | 53 | 5.49 | 0.25 | 6.65 (0.20) | 6.64 |
| SH(32) | SH32a | 9.76 | 1.12 | 316 | 28 (15) | 2.83 | 82 | 4.41 | 0.64 | 9.34 | 9.43 |

TABLE 2-continued

Detailed characteristics of the overall rotational diffusion of the proteins studied here, derived from the present analysis of $^{15}N$ relaxation data.

| Protein | Str.& | $\tau_1$(ns) | $D_\parallel/D_\perp$ | $\Phi°$ | $\Theta°$ | E/N† | Nr‡ | F§ | P∥(%) | $\tau_c$(ani) (ns) | $\tau_c$(iso) (ns) |
|---|---|---|---|---|---|---|---|---|---|---|---|
| unligated, both SH3&SH2 | | (0.17) | (0.05) | (41) | | | | | | (0.22) | |
| SH(32) ligated, both SH3&SH2 | SH32a | 11.22 (0.26) | 1.11 (0.06) | 169 (22) | 59 (23) | 1.89 | 83 | 2.42 | 7.2 | 10.82 (0.34) | 10.79 |

Table 2: Legend:

& The protein coordinate sets used here correspond to the following PDB entries: 1abo.pdb (labeled as SH3-I), 1abq.pdb (SH3-II), 2abl.pdb (SH32), and 1abl.pdb (SH2). For the sake of comparison, all considered structures were superimposed onto the SH3-I or the SH2 sets, for the analysis of the SH3 or SH2 domains, respectively, using the backbone atom coordinates for the core residues. The corresponding rotations in the case of the SH(32) structure are labeled as SH32a and SH32b, respectively. Hydrogen atoms were added to the crystal structure coordinates (1abo.pdb, 1abq.pdb, 2abl.pdb) using Insight II (MSI).

Numbers in parentheses indicate standard errors in the derived values.

† The target function E was normalized by the number of degrees of freedom, which in this analysis is $N=N_r-4$, where $N_r$ is the number of backbone amides used.

‡ Only those residues belonging to the well-defined secondary structure were used for the analysis. These comprise residues 66–72 (β1), 80–83(β2), 87–93 (β3), 99–104 (β4), 108–111(β5), and 117–119(β6) in the Abl SH3 and 133–141 (αI), 148–54 (βI), 160–167 (βII), 170–176 (βIII), 177–179 (βIV), 183–186 (βV), 190–193 (βVI), 194–205 (αβ), 209–213 (βVII), and 217–219 (βVIII) in Abl SH2. Of the core residues in the SH2 domain, 61, 59, and 59 residues were effectively resolved in the free SH2 and in the unligated and ligated SH(32), respectively. The corresponding numbers for SH3 domain are 30, 29, and 30. The following residues were excluded from the analysis, as either being influenced by conformational exchange or participating in slow motion, as indicated by their $R_2'/R_1'$ beyond two standard deviations from the mean. These were S134, R135, Q160, N193, T204, and A217 in the free SH2, Q160, R161, and S148 in the unligated, and R161, T178 in the ligated SH(32). Excluded from the analysis for the SH3 domain were I82 in the free SH3, L80, R89 in the unligated, and K87, R89, and W99 in the ligated SH(32).

§ F is the statistical F-test value assessing the statistical significance of the observed reduction in the target function when using the anisotropic model compared to the isotropic rotation model.

∥P is the percentile probability that the improvement in the fit using anisotropic rotational diffusion model versus the isotropic one could have occured by chance. P was obtained by applying the statistical F-test of E versus the corresponding value of the target function for the isotropic rotational diffusion model. The results indicate that for both unligated and ligated SH(32) the anisotropic model is statistically significant with a probability higher than 99%; the confidence level for the free domains is slightly lower (>95%). Similar results were obtained by assigning all $R_2'/R_1'$ values to random amides and comparing the resulting target function (averaged over 500 of the scrambled data sets) with the one obtained by direct, anisotropic fit.

¶ $\tau_c$ (ani) was calculated as $\tau_c=3\tau_1/(D_\parallel/D_\perp+2)$, where $t_1$ and $D_\parallel/D_\perp$ were derived from orientational dependence of $R_2'/R_1'$ for the core residues.

$\tau_c$ (iso) shown in this column was determined by fitting the $R_2'/R_1'$ data to the isotropic rotational diffusion model for the core residues.

Figure 3:
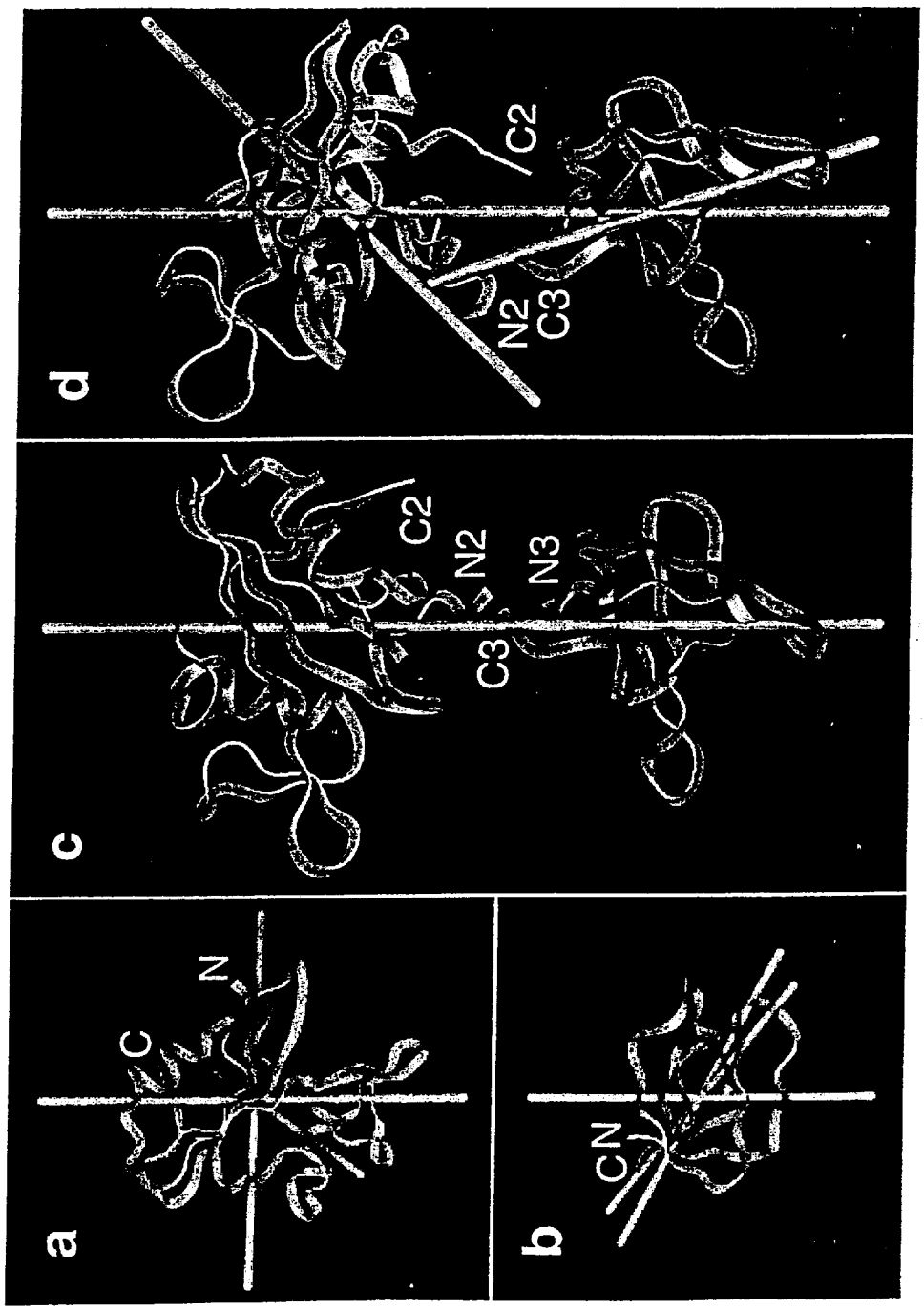
FIG. 3a–3d show the experimental orientation of the rotational diffusion axes with respect to the domain structures. Shown are single (FIG. 3a) SH2 and ((FIG. 3b) SH3 domains, and the reconstructed relative orientation of the two domains in the (FIG. 3c) unligated and (FIG. 3d) ligated Abl SH(32). The structure of protein backbone is represented by ribbons colored green for the SH2 and blue for the SH3; the N- and C-termini are indicated. For each domain, rods represent orientations of the unique diffusion axis (corresponding to the parallel component D$_\parallel$of the rotational diffusion tensor) in the case of the free domain (white) and in the dual domain construct, unligated (gold) and ligated (pink). Relative orientation of the individual domains in the dual domain construct was obtained by aligning the corresponding diffusion axes, as shown in parts FIGS. 3c and 3d. The angle of rotation of each domain around its diffusion axis cannot be determined from these data, because of the assumed axial symmetry of the model. A rhombohedral fitting can be done with very high precision data [Clore et al., *J. Am. Chem. Soc.*, 120:4889–90 (1998)]. In the ligated SH(32), the orientation shown was chosen to ensure proximal positioning of the ligand binding sites of the two domains (residues implicated in binding are colored red). Also shown in FIG. 3d, for comparison, are orientations of the diffusion axes of the two domains as they are in the unligated SH(32). The observed change in orientation of the overall rotation axis upon ligation is 15° for the SH3, and 47° for the SH2 parts of the dual domain construct. The same optimization procedure applied to the crystal structure of Abl SH(32), [Nam et al., *Structure*, 4:1105–1114 (1996)], including the R$_2$'/R$_1$' data for both SH2 and SH3 domains simultaneously, resulted in the normalized target function E/N, which is 2.8 times greater than the corresponding values obtained here. The low probability 6×10$^{-6}$, that this difference could have occurred by chance indicates differences in the relative orientations of the domains between crystal and solution studies.

The orientation of the principal axes of the rotational diffusion tensor with respect to the protein coordinate frame and the principal values of the tensor were determined from the measured $R_2'/R_1'$ values, as described in Materials and Methods, above (see also below). The observed rotational anisotropies for the free SH3 and SH2 domains are consistent with the ratios of the rotational diffusion tensor components, 1.14:1.02:1 and 1.17:1.04:1, respectively, calculated using the bead-method [de la Torre and Bloomfield, *Q. Rev. Biophys*, 14:81–139 (1981); and McDonnell et al., *J. Mol. Biol.*, 279:921–928 (1998)]. Table 1 and FIG. 3 show changes in both the magnitude and orientation of the rotational diffusion tensor for each of the domains between the free state and the dual domain construct. The orientation of the diffusion axes sensed by the individual domains in the free SH(32) is consistent with the elongated conformation of the dual domain construct (FIG. 3c). The relative orientation of the two domains in the SH(32)/Ligand complex (FIG. 3d), reconstructed from the present data, differs significantly, consistent with substantial changes in the overall spatial arrangement of the domains, induced by the consolidated ligand. A fluorophore probe inserted in Abl SH(32) [Cotton et al., *J. Am. Chem. Soc.*, 121:1100–1 (1999)] also senses a change in conformation on ligation. Either orientation in solution is incompatible with that observed in the crystalline state [Nam et al., *Structure*, 4:1105–1114 (1996)]. The simplest assumption is that the crystal state is different from that in solution.

The approach used here assumes that the dual domain protein can be represented by a prolate ellipsoid of revolution. The analysis used here cannot absolutely distinguish between prolate or oblate ellipsoid models [Blackledge et al., *J. Am. Chem. Soc.*, 120:4538–39 (1998)]. In addition, the effects of rhombicity of the rotational diffusion tensor on relaxation, and averaging effects from different time scales of motion are ignored. With regard to rhombicity, its inclusion in calculations using residual dipolar couplings has been illustrated [Clore et al., *J. Magn. Reson.*, 131:159–62 (1998)] and could be incorporated in the current analysis, by generalization to three axes of Eqn [1].

With regard to time dependencies, the observed rotational anisotropy ($D_\parallel/D\perp$) of the dual domain is somewhat lower than expected from rigid-body models [Koenig, Biopolymers, 14:2421–2423 (1975)] (e.g., compared to $D_\parallel/D_\perp=1.87$ for a prolate ellipsoid of revolution with the axial ratio of 2:1), presumably the observed values are averaged by interdomain dynamics on the NMR time scale (10 ns to 100 ms). This is consistent with the different degrees of rotational anisotropy for individual domains; the $D_\parallel/D_\perp$ values for SH2 are somewhat smaller than for the SH3 part. Even in the SH(32)/ligand complex, where the average characteristics ($\tau_c$, $\tau_{app}$) of rotational diffusion for the two domains are similar, their apparent anisotropies are somewhat different, possibly due to flexibility of the ligand itself or by interconversion between bivalent and monovalent ligated forms. Similar interpretations involving interdomain mobility were reported earlier [Bruschweiler et al., *Science*, 268:886–9 (1995); Hansen et al., *Biochemistry*, 33:15418–15424 (1994); and Barbato et al., *Biochemistry*, 31:5269–78 (1992)]. The present results demonstrate that the relative orientation of SH2 and SH3 domains in Abl SH(32) is not fixed, and can be changed by the protein interaction with a consolidated ligand. Ligand binding studies [Xu et al., *Biochemistry*, 38:3491–97 (1999)] suggest flexibility of the dual domain SH(32) construct to accommodate several relative orientations of the binding sites.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. A method for determining the relative orientation of two or more selected components of a macromolecule in solution with respect to the global molecular coordinate frame of the macromolecule comprising:

(a) determining the orientation of the molecular frame for the selected components of the macromolecule in solution, thereby determining a set of rotational diffusion axes for the selected components; wherein the macromolecule comprises two or more components; and (b) determining the inter-component orientation in the macromolecule based on the orientation of the selected components with respect to the global molecular coordinate frame, and aligning the set of rotational diffusion axes of the component; wherein the relative orientation of the selected components of the macromolecule with respect to the global molecular coordinate frame of the macromolecule is determined.

2. The method of claim 1 wherein said determining of the orientation of the molecular frame for the selected components of the macromolecule comprises determining the orientation of the overall rotational diffusion tensor as seen by each of the selected components.

3. The method of claim 1 wherein determining the orientation of the molecular frame for the selected components of the macromolecule in solution includes:

(i) measuring the relaxation rate of a heteronuclear bond contained by at least one of the selected components; and (ii) deriving the overall hydrodynamic characteristics and the local internuclear vector orientation of the selected component(s) containing the heteronuclear bond.

4. The method of claim 3 wherein the heteronuclear bond is selected from the group consisting of a hydrogen—carbon-13 bond, a hydrogen—nitrogen-15 bond, a deuterium—carbon-13 bond, a deuterium—nitrogen-15 bond, a tritium—carbon-13 bond, and a tritium—nitrogen-15 bond.

5. The method of claim 4 wherein the individual component is a peptide having amide bonds; and the measuring of the relaxation rate of the heteronuclear bond contained by the peptide comprises measuring the $^{15}N$ relaxation rates for the individual amides of the peptide.

6. The method of claim 5 wherein the macromolecule is prepared by segmental isotopic labeling.

7. The method of claim 1 wherein the macromolecule is a polymer selected from the group consisting of a biopolymer, a synthetic chemical polymer; and a chimeric polymer.

8. The method of claim 7 wherein the polymer is a biopolymer selected from the group consisting of a peptide, a protein, a carbohydrate and a nucleic acid.

9. A method of determining the change in orientation of two or more selected components of a macromolecule in solution upon binding of a ligand to the macromolecule comprising:

(a) measuring the relaxation rate of a heteronuclear bond contained by a selected component in the presence of a ligand for the macromolecule under conditions that the ligand binds to the macromolecule; wherein the macromolecule comprises two or more components;

(b) measuring the relaxation rate of the heteronuclear bond in the absence of the ligand under the same conditions as step (a); and (c) deriving the overall hydrodynamic characteristics and the local internuclear vector orientation of the selected components of the macromolecule for steps (a) and (b); wherein the change in orientation of the selected components of the macromolecule in solution upon binding of the ligand is determined.

10. The method of claim 9 wherein the heteronuclear bond is selected from the group consisting of a hydrogen—carbon-13 bond, a hydrogen—nitrogen-15 bond, a deuterium—carbon-13 bond, a deuterium—nitrogen-15 bond, a tritium—carbon-13 bond, and a tritium—nitrogen-15 bond.

11. The method of claim 9 further comprising the steps of measuring the relaxation rate of the heteronuclear bond of the selected component in the absence of the rest of the macromolecule under the same conditions as step (a) in the absence of the ligand.

12. The method of claim 9 further comprising the step of measuring the relaxation rate of the heteronuclear bond of the selected component in the absence of the rest of the macromolecule under the same conditions as step (a) but in the presence of the ligand.

13. The method of claim 9 further comprising determining the contributions from high frequency components of local motion from the relaxation rates of the heteronuclear bond and subtracting said contributions from the relaxation rates of the heteronuclear bond.

14. The method of claim 9 wherein the macromolecule is a polymer selected from the group consisting of a biopolymer, a synthetic chemical polymer; and a chimeric polymer.

15. The method of claim 14 wherein the polymer is a biopolymer selected from the group consisting of a peptide, a protein, a carbohydrate and a nucleic acid.

16. The method of claim 9 wherein the macromolecule comprises as a component a peptide having amide bonds; and said measuring of the relaxation rate of the heteronuclear bond contained by the peptide comprises measuring the $^{15}$N relaxation rates for the individual amides of the peptide.

17. The method of claim 9 wherein the macromolecule is prepared by segmental isotopic labeling.

18. The method of claim 9 wherein the ligand is a consolidated ligand.

19. A method of identifying an agent that effects the orientation of selected components of a macromolecule in solution comprising:

(a) measuring the relaxation rate of a heteronuclear bond contained by a selected component of the macromolecule in solution in the presence of an agent that can potentially effect the orientation of selected components of the macromolecule; wherein the macromolecule comprises two or more components;

(b) measuring the relaxation rate of the heteronuclear bond in the absence of the agent under the same conditions as step (a);

(c) deriving the overall hydrodynamic characteristics and the local internuclear vector orientation of the selected components of the macromolecule for steps (a) and (b); and (d) determining whether there is a change in orientation of the selected components of the macromolecule in solution in the presence of the agent; wherein when a change in orientation is determined, the agent is identified as an agent that effects the orientation of selected components of the macromolecule in solution.

20. The method of claim 19 wherein the macromolecule is a protein and the agent identified is a potential agonist or antagonist of the protein.

21. The method of claim 20 wherein the protein is a multi-domain protein.

22. The method of claim 19 wherein the macromolecule comprises a DNA binding protein bound to its nucleic acid binding site and the agent identified is a potential agonist or antagonist of the DNA binding protein-nucleic acid interaction.

\* \* \* \* \*